US009675659B2

(12) United States Patent
Ryckman et al.

(10) Patent No.: US 9,675,659 B2
(45) Date of Patent: Jun. 13, 2017

(54) METHODS OF TREATING LUNG INFECTION WITH CASPOFUNGIN

(71) Applicant: Trilogy Therapeutics, Inc., San Diego, CA (US)

(72) Inventors: David M. Ryckman, San Diego, CA (US); Iching G. Yu, San Diego, CA (US)

(73) Assignee: Trilogy Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/241,645

(22) Filed: Aug. 19, 2016

(65) Prior Publication Data

US 2017/0049846 A1 Feb. 23, 2017

Related U.S. Application Data

(60) Provisional application No. 62/208,396, filed on Aug. 21, 2015.

(51) Int. Cl.
A61K 9/14 (2006.01)
A61K 38/08 (2006.01)
A61K 9/00 (2006.01)

(52) U.S. Cl.
CPC ............ *A61K 38/08* (2013.01); *A61K 9/0075* (2013.01)

(58) Field of Classification Search
None
See application file for complete search history.

(56) References Cited

U.S. PATENT DOCUMENTS

| | | | |
|---|---|---|---|
| 4,496,086 A | 1/1985 | Duchadeau | |
| 5,280,784 A | 1/1994 | Kohler | |
| 5,309,900 A | 5/1994 | Knoch et al. | |
| 5,312,046 A | 5/1994 | Knoch et al. | |
| 5,378,804 A | 1/1995 | Balkovec et al. | |
| 5,458,136 A | 10/1995 | Jaser et al. | |
| 5,461,695 A | 10/1995 | Knoch | |
| 5,549,102 A | 8/1996 | Lintl et al. | |
| 5,740,966 A | 4/1998 | Blaha-Schnabel | |
| 5,936,062 A | 8/1999 | Leonard et al. | |
| 5,952,300 A | 9/1999 | Nerurkar et al. | |
| 5,957,389 A | 9/1999 | Wunderlich et al. | |
| 6,000,394 A | 12/1999 | Blaha-Schnabel | |
| 6,085,741 A | 7/2000 | Becker | |
| 6,176,237 B1 | 1/2001 | Wunderlich et al. | |
| 6,513,519 B2 | 2/2003 | Gallem | |
| 6,513,727 B1 | 2/2003 | Jaser et al. | |
| 2006/0025355 A1* | 2/2006 | Duddu ................ | A61K 9/0075 514/28 |
| 2008/0035141 A1* | 2/2008 | Warner ................ | A61K 31/56 128/200.14 |
| 2009/0170753 A1 | 7/2009 | Welz et al. | |
| 2010/0137197 A1 | 6/2010 | Mittal et al. | |
| 2010/0184696 A1 | 7/2010 | O'Neil | |
| 2014/0014094 A1 | 1/2014 | Warner et al. | |
| 2014/0128315 A1* | 5/2014 | He ........................ | C07K 7/56 514/3.3 |

FOREIGN PATENT DOCUMENTS

WO WO 2005082054 A2 * 9/2005 ............. A01N 25/00

OTHER PUBLICATIONS

Berge et al. Pharmaceutical Salts. Journal of Pharmaceutical Sciences 66(1):1-19 (Jan. 1977).
Cicogna et al. Efficacy of prophylactic aerosol amphotericin B lipid complex in a rat model of pulmonary aspergillosis. Antimicrob Agents Chemother 41(2):259-261 (1997).
Damle et al. Pharmacokinetics and Tissue Distribution of Anidulafungin in Rats. Antimicrob. Agents Chemo 52:2673-2676 (2008).
Espinel-Ingroff et al. Wild-Type MIC Distributions and Epidemiological Cutoff Values for Amphotericin B and *aspergillus* spp. for the CLSI Broth Microdilution Method (M38-A2 Document). Antimicrob Agents Chemo 55(6):2855-2858 (2011).
Hadju et al. Preliminary Animal Pharmacokinetics of the Parenteral Antifungal Agent MK-0991 (L-743,872). Antimicrob Agents Chemo 41(11):2339-2344 (1997).
Niwa et al. Tissue Distribution after Intravenous Dosing of Micafungin, an Antifungal Drug, to Rats. Bio Pharm Bull 27(7):1154-1156 (2004).
Pfaller et al. Correlation of MIC with Outcome for Candida Species Tested against Caspofungin, Anidulafungin, and Micafungin: Analysis and Proposal for Interpretive MIC Breakpoints. J Clin Microbiol 46(8):2620-2629 (2008).
Sandhu et al. Disposition of Caspofungin, a Novel Antifungal Agent, in Mice, Rats, Rabbits, and Monkeys. Antimicrob Agents Chemo 48(4):1272-1280 (2004).
Stone et al. Disposition of Caspofungin: Role of Distribution in Determining Pharmacokinetics in Plasma. Antimicrob Agents Chemo 48(3):815-823 (2004).
Van De Sande et al. Caspofungin prolongs survival of transiently neutropenic rats with advanced-stage invasive pulmonary aspergillosis. Antimicrob Agents Chemother 52(4):1345-1350 (2008).
Cancidas® (caspofungin acetate) Product label. Merck & Co., Inc. (18 pgs) (2001).
PCT/US2016/047735 International Search Report and Written Opinion dated Nov. 7, 2016.
Shivanand et al. Formulation and Evaluation of Insulin Dry Powder for Pulmonary Delivery. International Journal of PharmTech Research 1(4):1182-1189 (2009).

\* cited by examiner

*Primary Examiner* — Susan Tran
(74) *Attorney, Agent, or Firm* — Wilson Sonsini Goodrich & Rosati

(57) ABSTRACT

Methods for the treatment and/or prevention of a fungal infection in the pulmonary system of a subject in need thereof with caspofungin or a derivative thereof are disclosed herein.

28 Claims, 4 Drawing Sheets

METHODS OF TREATING LUNG INFECTION WITH CASPOFUNGIN

CROSS REFERENCE

Figure 1:
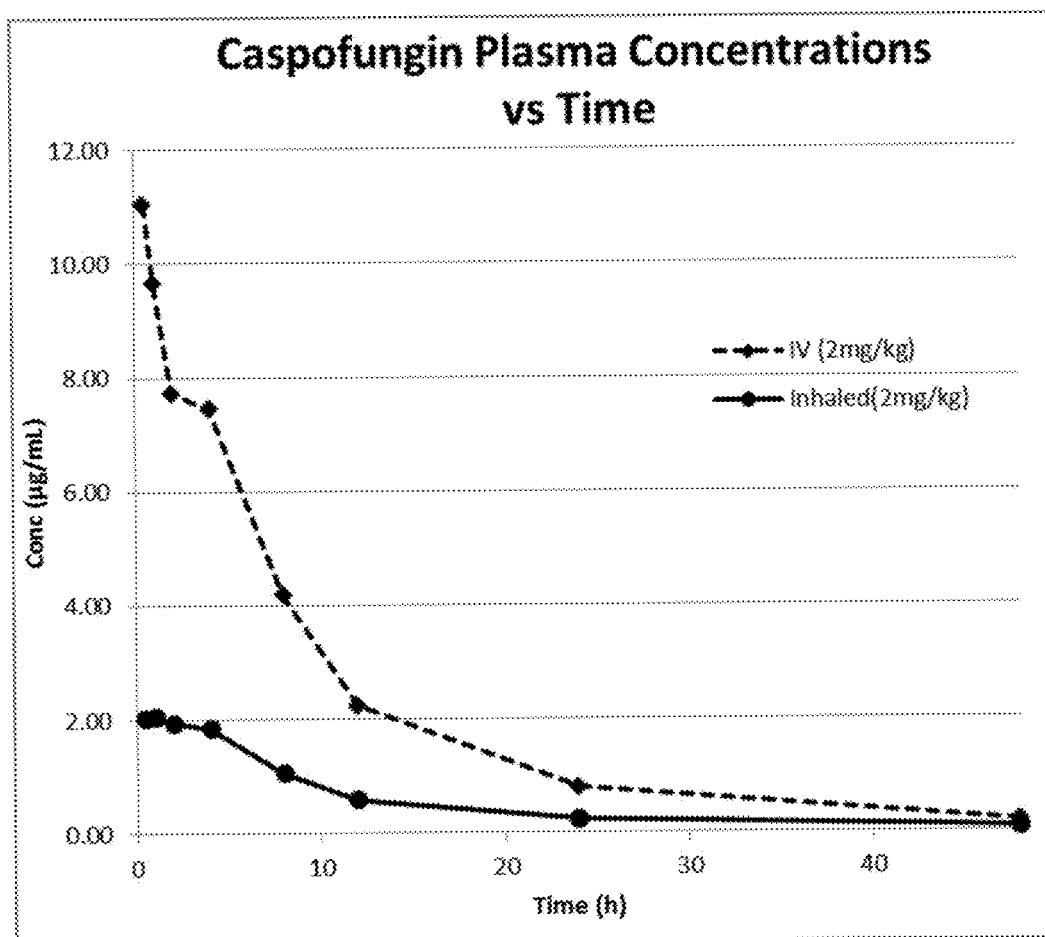

This application claims the benefit of U.S. Provisional Application No. 62/208,396, filed Aug. 21, 2015, the contents of which is hereby incorporated by reference in its entirety.

BACKGROUND

A pulmonary infection caused by *Aspergillus* species is a serious invasive infection that usually occurs in people with compromised immune systems due to cancer, AIDS, leukemia, an organ transplant, chemotherapy, or other conditions or medications that lower the number or function of normal white blood cells or weaken the immune system. The usual course of treatment requires the intravenous or oral use of antifungal agents.

SUMMARY OF THE DISCLOSURE

Provided herein is a method of preventing or treating a fungal infection in the pulmonary system of a subject in need thereof comprising administering to the subject an inhalation composition comprising caspofungin, or a polymorph, pharmaceutically acceptable salt, hydrate, or solvate thereof, wherein the inhalation composition is essentially free of mannitol.

In some embodiments, the inhalation composition is essentially free of sugar alcohol. In some embodiments, the inhalation composition is essentially free of sugar alcohol or sugar. In some embodiments, the pharmaceutically acceptable salt of caspofungin is the acetate.

In some embodiments, the administration of the inhalation composition provides a lung tissue concentration of caspofungin or the polymorph, pharmaceutically acceptable salt, hydrate, or solvate thereof that is from about 1-fold to about 100-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 50-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 1-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 10-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 20-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 30-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 40-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 50-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 60-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 70-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 80-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 90-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 100-fold greater than the concentration in the lung via intravenous administration at the same delivery dose.

In some embodiments, the lung tissue concentration of caspofungin or the polymorph, pharmaceutically acceptable salt, hydrate, or solvate thereof is greater than the concentration in the lung via intravenous administration at the same delivery dose for about 0.5 hour to about 168 hours.

In some embodiments, the administration of the inhalation composition provides a concentration of caspofungin or the polymorph, pharmaceutically acceptable salt, hydrate, or solvate thereof in the lung that is from about 1-fold greater to about 1000-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 1-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 2-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 3-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 4-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 5-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 10-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 15-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 20-fold greater than the concentration in liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 50-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 70-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 100-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 500-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 1000-fold greater than the concentration in the liver, kidney, spleen, pancreas or plasma.

In some embodiments, the concentration of caspofungin or the polymorph, pharmaceutically acceptable salt, hydrate, or solvate thereof in the lung is greater than the concentration in the liver, kidney, spleen, pancreas or plasma for about 0.5 hour to about 168 hours.

In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 3 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 6 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 12 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 24 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 48 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 72 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 96 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 120 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 168 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 336 hours after administration.

In some embodiments, the minimum inhibitory concentration (MIC) is from about 0.001 µg/mL to about 128 µg/mL. In some embodiments, the minimum inhibitory concentration (MIC) is from about 0.001 µg/mL to about 32 µg/mL. In some embodiments, the minimum inhibitory concentration (MIC) is from about 0.001 µg/mL to about 16 µg/mL. In some embodiments, the minimum inhibitory concentration (MIC) is from about 0.125 µg/mL to about 128 µg/mL. In some embodiments, the minimum inhibitory concentration (MIC) is from about 0.125 µg/mL to about 32 µg/mL. In some embodiments, the minimum inhibitory concentration (MIC) is from about 0.25 µg/mL to about 16 µg/mL. In some embodiments, the minimum inhibitory concentration (MIC) is from about 0.25 µg/mL to about 32 µg/mL. In some embodiments, the minimum inhibitory concentration (MIC) is from about 16 µg/mL to about 128 µg/mL. In some embodiments, the minimum inhibitory concentration (MIC) is about 0.001 µg/mL. In some embodiments, the minimum inhibitory concentration (MIC) is about 0.005 µg/mL. In some embodiments, the minimum inhibitory concentration (MIC) is about 0.010 µg/mL. In some embodiments, the minimum inhibitory concentration (MIC) is about 0.015 µg/mL. In some embodiments, the minimum inhibitory concentration (MIC) is about 0.020 µg/mL. In some embodiments, the minimum inhibitory concentration (MIC) is about 0.030 µg/mL. In some embodiments, the minimum inhibitory concentration (MIC) is about 0.040 µg/mL. In some embodiments, the minimum inhibitory concentration (MIC) is about 0.050 µg/mL. In some embodiments, the minimum inhibitory concentration (MIC) is about 0.060 µg/mL. In some embodiments, the minimum inhibitory concentration (MIC) is about 0.100 µg/mL. In some embodiments, the minimum inhibitory concentration (MIC) is about 0.125 µg/mL. In some embodiments, the minimum inhibitory concentration (MIC) is about 0.25 µg/mL. In some embodiments, the minimum inhibitory concentration (MIC) is about 0.30 µg/mL. In some embodiments, the minimum inhibitory concentration (MIC) is about 0.50 µg/mL. In some embodiments, the minimum inhibitory concentration (MIC) is about 0.75 µg/mL. In some embodiments, the minimum inhibitory concentration (MIC) is about 1.00 µg/mL. In some embodiments, the minimum inhibitory concentration (MIC) is about 2.00 µg/mL. In some embodiments, the minimum inhibitory concentration (MIC) is about 4.00 µg/mL. In some embodiments, the minimum inhibitory concentration (MIC) is about 8.00 µg/mL. In some embodiments, the minimum inhibitory concentration (MIC) is about 16.00 µg/mL. In some embodiments, the minimum inhibitory concentration (MIC) is about 32.00 µg/mL. In some embodiments, the minimum inhibitory concentration (MIC) is about 128.00 µg/mL.

In some embodiments, the minimum effective concentration (MEC) is from about 0.001 µg/mL to about 128 µg/mL. In some embodiments, the minimum effective concentration (MEC) is from about 0.001 µg/mL to about 32 µg/mL. In some embodiments, the minimum effective concentration (MEC) is from about 0.001 µg/mL to about 16 µg/mL. In some embodiments, the minimum effective concentration (MEC) is from about 0.001 µg/mL to about 0.6 µg/mL. In some embodiments, the minimum effective concentration (MEC) is from about 0.008 µg/mL to about 0.6 µg/mL. In some embodiments, the minimum effective concentration (MEC) is about 0.001 µg/mL. In some embodiments, the minimum effective concentration (MEC) is about 0.005 µg/mL. In some embodiments, the minimum effective concentration (MEC) is about 0.010 µg/mL. In some embodiments, the minimum effective concentration (MEC) is about 0.015 µg/mL. In some embodiments, the minimum effective concentration (MEC) is about 0.020 µg/mL. In some embodiments, the minimum effective concentration (MEC) is about 0.030 µg/mL. In some embodiments, the minimum effective concentration (MEC) is about 0.040 µg/mL. In some embodiments, the minimum effective concentration (MEC) is about 0.050 µg/mL. In some embodiments, the minimum effective concentration (MEC) is about 0.060 µg/mL. In some embodiments, the minimum effective concentration (MEC) is about 0.100 µg/mL. In some embodiments, the minimum effective concentration (MEC) is about 0.125 µg/mL. In some embodiments, the minimum effective concentration (MEC) is about 0.250 µg/mL. In some embodiments, the minimum effective concentration (MEC) is about 0.300 µg/mL. In some embodiments, the minimum effective concentration (MEC) is about 0.500 µg/mL. In some embodiments, the minimum effective concentration (MEC) is about 0.75 µg/mL. In some embodiments, the minimum effective concentration (MEC) is about 1.00 µg/mL. In some embodiments, the minimum effective concentration (MEC) is about 2.00 µg/mL. In some embodiments, the minimum effective concentration (MEC) is about 4.00 µg/mL. In some embodiments, the minimum effective concentration (MEC) is about 8.00 µg/mL. In some embodiments, the minimum effective concentration (MEC) is about 16.00 µg/mL. In some embodiments, the minimum effective concentration (MEC) is about 32.00 µg/mL. In some embodiments, the minimum effective concentration (MEC) is about 128.00 µg/mL.

In some embodiments, the inhalation composition is administered with an inhalation device selected from a jet nebulizer, ultrasonic wave nebulizer, high efficiency nebulizer, heat vaporizer, soft mist inhaler, thermal aerosol inhaler, or electrohydrodynamic-based solution misting inhaler. In some embodiments, the inhalation device is a jet nebulizer. In some embodiments, the inhalation device is an ultrasonic wave nebulizer.

In some embodiments, the inhalation composition is administered by the inhalation device as droplets or particles having a mass median aerodynamic diameter (MMAD) from about 1 μm to about 10 μm. In some embodiments, the inhalation composition is administered by the inhalation device as droplets or particles having a mass median aerodynamic diameter (MMAD) from about 1 μm to about 5 μm. In some embodiments, the inhalation composition is administered by the inhalation device as droplets or particles having a mass median aerodynamic diameter (MMAD) from about 2 μm to about 3 μm. In some embodiments, the half-life of the caspofungin, or a polymorph, pharmaceutically acceptable salt, hydrate, or solvate thereof in the lung is about 1 hour to about 50 hours. In some embodiments, the half-life of the caspofungin, or a polymorph, pharmaceutically acceptable salt, hydrate, or solvate thereof in the lung is about 20 hours to about 50 hours.

In some embodiments, the inhalation composition is stable from at about −20° C. to about 25° C. In some embodiments, the inhalation composition is stable from at about 5° C. to about 25° C. In some embodiments, the inhalation composition is stable at about 25° C. In some embodiments, the inhalation composition is stable for at least about 6 months to about 2 years. In some embodiments, the inhalation composition has a pH from about 4.0 to about 7.5. In some embodiments, the inhalation composition has a pH from about 4.0 to about 8.5. In some embodiments, the inhalation composition has a pH from about 5.0 to about 8.5. In some embodiments, the inhalation composition has a pH from about 6.0 to about 7.5. In some embodiments, the inhalation composition has a pH from about 7.0 to about 7.5.

In some embodiments, the method is for treating a fungal infection caused by *Candida* sp., and/or by *Aspergillus* sp., and/or by *Pneumocystis jirovecii*. In some embodiments, the method is for treating a fungal infection caused by *Candida albicans, Candida tropicalis, Candida krusei*, or *Candida glabrata*. In some embodiments, the method is for treating a fungal infection caused by *Aspergillus fumigatus, Aspergillus flavus*, or *Aspergillus niger*. In some embodiments, the method is for preventing a fungal infection caused by *Candida* sp., and/or by *Aspergillus* sp., and/or by *Pneumocystis jirovecii*. In some embodiments, the method is for preventing a fungal infection caused by *Candida albicans, Candida tropicalis, Candida krusei*, or *Candida glabrata*. In some embodiments, the method is for preventing a fungal infection caused by *Aspergillus fumigatus, Aspergillus flavus*, or *Aspergillus niger.*

In some embodiments, the subject is immunocompromised. In some embodiments, the subject is a transplant recipient or a subject undergoing cancer chemotherapy. In some embodiments, the subject is a recipient of a hematopoietic stem-cell transplant, bone marrow transplant, lung transplant, liver transplant, heart transplant, kidney transplant, pancreas transplant or a combination thereof.

Also provided here is a kit comprising: a composition suitable for administration via inhalation, wherein the composition comprises caspofungin, or a polymorph, pharmaceutically acceptable salt, hydrate, or solvate thereof, and wherein the composition is essentially free of mannitol; and an inhalation device. In some embodiments, the administration of the composition provides a lung tissue concentration of caspofungin or the polymorph, pharmaceutically acceptable salt, hydrate, or solvate thereof that is from about 1-fold to about 100-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 50-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 1-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 10-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 20-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 30-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 40-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 50-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 60-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 70-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 80-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 90-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 100-fold greater than the concentration in the lung via intravenous administration at the same delivery dose.

In some embodiments, the lung tissue concentration of caspofungin or the polymorph, pharmaceutically acceptable salt, hydrate, or solvate thereof is greater than the concentration in the lung via intravenous administration at the same delivery dose for about 0.5 hour to about 168 hours.

In some embodiments, the administration of the composition provides a concentration of caspofungin or the polymorph, pharmaceutically acceptable salt, hydrate, or solvate thereof in the lung that is from about 1-fold greater to about 1000-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 1-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 2-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 3-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 4-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 5-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 10-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 15-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 20-fold greater than the concentration in liver, kidney, spleen, pancreas or plasma. In some embodiments, the administration of the composition provides a concentration of caspofungin or the polymorph, pharmaceutically acceptable salt, hydrate, or solvate thereof in the lung that is about 50-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 70-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 100-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 500-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 1000-fold greater than the concentration in the liver, kidney, spleen, pancreas or plasma In some embodiments, the concentration of caspofungin or the polymorph, pharmaceutically acceptable salt, hydrate, or solvate thereof in the lung is greater than the concentration in the liver, kidney, spleen, pancreas or plasma for about 0.5 hour to about 168 hours.

In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 3 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 6 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 12 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 24 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 48 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 72 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 96 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 120 hours after administration. In some embodiments the concentration of caspofungin or the polymorph, pharmaceutically acceptable salt, hydrate, or solvate thereof in the lung is above the minimum inhibitory concentration (MIC) or the minimum effective concentration (MEC) for about 168 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 336 hours after administration.

In some embodiments, the minimum inhibitory concentration (MIC) is from about 0.001 μg/mL to about 128 μg/mL. In some embodiments, the minimum inhibitory concentration (MIC) is from about 0.001 μg/mL to about 32 μg/mL. In some embodiments, the minimum inhibitory concentration (MIC) is from about 0.001 μg/mL to about 16 μg/mL. In some embodiments, the minimum inhibitory concentration (MIC) is from about 0.125 μg/mL to about 128 μg/mL. In some embodiments, the minimum inhibitory concentration (MIC) is from about 0.125 μg/mL to about 32 μg/mL. In some embodiments, the minimum inhibitory concentration (MIC) is from about 0.25 μg/mL to about 16 μg/mL. In some embodiments, the minimum inhibitory concentration (MIC) is from about 0.25 μg/mL to about 32 μg/mL. In some embodiments, the minimum inhibitory concentration (MIC) is from about 16 μg/mL to about 128 μg/mL. In some embodiments, the minimum inhibitory concentration (MIC) is about 0.001 μg/mL. In some embodiments, the minimum inhibitory concentration (MIC) is about 0.005 μg/mL. In some embodiments, the minimum inhibitory concentration (MIC) is about 0.010 μg/mL. In some embodiments, the minimum inhibitory concentration (MIC) is about 0.015 μg/mL. In some embodiments, the minimum inhibitory concentration (MIC) is about 0.020 μg/mL. In some embodiments, the minimum inhibitory concentration (MIC) is about 0.030 μg/mL. In some embodiments, the minimum inhibitory concentration (MIC) is about 0.040 μg/mL. In some embodiments, the minimum inhibitory concentration (MIC) is about 0.050 μg/mL. In some embodiments, the minimum inhibitory concentration (MIC) is about 0.060 μg/mL. In some embodiments, the minimum inhibitory concentration (MIC) is about 0.100 μg/mL. In some embodiments, the minimum inhibitory concentration (MIC) is about 0.125 μg/mL. In some embodiments, the minimum inhibitory concentration (MIC) is about 0.25 μg/mL. In some embodiments, the minimum inhibitory concentration (MIC) is about 0.30 μg/mL. In some embodiments, the minimum inhibitory concentration (MIC) is about 0.50 μg/mL. In some embodiments, the minimum inhibitory concentration (MIC) is about 0.75 μg/mL. In some embodiments, the minimum inhibitory concentration (MIC) is about 1.00 μg/mL. In some embodiments, the minimum inhibitory concentration (MIC) is about 2.00 μg/mL. In some embodiments, the minimum inhibitory concentration (MIC) is about 4.00 μg/mL. In some embodiments, the minimum inhibitory concentration (MIC) is about 8.00 μg/mL. In some embodiments, the minimum inhibitory concentration (MIC) is about 16.00 μg/mL. In some embodiments, the minimum inhibitory concentration (MIC) is about 32.00 μg/mL. In some embodiments, the minimum inhibitory concentration (MIC) is about 128.00 μg/mL.

In some embodiments, the minimum effective concentration (MEC) is from about 0.001 µg/mL to about 128 µg/mL. In some embodiments, the minimum effective concentration (MEC) is from about 0.001 µg/mL to about 32 µg/mL. In some embodiments, the minimum effective concentration (MEC) is from about 0.001 µg/mL to about 16 µg/mL. In some embodiments, the minimum effective concentration (MEC) is from about 0.001 µg/mL to about 0.6 µg/mL. In some embodiments, the minimum effective concentration (MEC) is from about 0.008 µg/mL to about 0.6 µg/mL. In some embodiments, the minimum effective concentration (MEC) is about 0.001 µg/mL. In some embodiments, the minimum effective concentration (MEC) is about 0.005 µg/mL. In some embodiments, the minimum effective concentration (MEC) is about 0.010 µg/mL. In some embodiments, the minimum effective concentration (MEC) is about 0.015 µg/mL. In some embodiments, the minimum effective concentration (MEC) is about 0.020 µg/mL. In some embodiments, the minimum effective concentration (MEC) is about 0.030 µg/mL. In some embodiments, the minimum effective concentration (MEC) is about 0.040 µg/mL. In some embodiments, the minimum effective concentration (MEC) is about 0.050 µg/mL. In some embodiments, the minimum effective concentration (MEC) is about 0.060 µg/mL. In some embodiments, the minimum effective concentration (MEC) is about 0.100 µg/mL. In some embodiments, the minimum effective concentration (MEC) is about 0.125 µg/mL. In some embodiments, the minimum effective concentration (MEC) is about 0.250 µg/mL. In some embodiments, the minimum effective concentration (MEC) is about 0.300 µg/mL. In some embodiments, the minimum effective concentration (MEC) is about 0.500 µg/mL. In some embodiments, the minimum effective concentration (MEC) is about 0.75 µg/mL. In some embodiments, the minimum effective concentration (MEC) is about 1.00 µg/mL. In some embodiments, the minimum effective concentration (MEC) is about 2.00 µg/mL. In some embodiments, the minimum effective concentration (MEC) is about 4.00 µg/mL. In some embodiments, the minimum effective concentration (MEC) is about 8.00 µg/mL. In some embodiments, the minimum effective concentration (MEC) is about 16.00 µg/mL. In some embodiments, the minimum effective concentration (MEC) is about 32.00 µg/mL. In some embodiments, the minimum effective concentration (MEC) is about 128.00 µg/mL.

In some embodiments, the inhalation device selected from a jet nebulizer, ultrasonic wave nebulizer, high efficiency nebulizer, heat vaporizer, soft mist inhaler, thermal aerosol inhaler, or electrohydrodynamic-based solution misting inhaler. In some embodiments, the inhalation device is a jet nebulizer. In some embodiments, the inhalation device is an ultrasonic wave nebulizer.

In some embodiments, the composition is capable of being administered by the inhalation device as droplets or particles having a mass median aerodynamic diameter (MMAD) of about 1 μm to about 10 μm. In some embodiments, the composition is capable of being administered by the inhalation device as droplets or particles having a mass median aerodynamic diameter (MMAD) of about 1 μm to about 5 μm. In some embodiments, the composition is capable of being administered by the inhalation device as droplets or particles having a mass median aerodynamic diameter (MMAD) of about 2 μm to about 3 μm. In some embodiments, the half-life of the caspofungin, or a polymorph, pharmaceutically acceptable salt, hydrate, or solvate thereof in the lung is about 1 hour to about 50 hours. In some embodiments, the half-life of the caspofungin, or a polymorph, pharmaceutically acceptable salt, hydrate, or solvate thereof in the lung is about 20 hours to about 50 hours.

In some embodiments, the inhalation composition is stable from at about −20° C. to about 25° C. In some embodiments, the composition is stable from at about 5° C. to about 25° C. In some embodiments, the composition is stable at about 25° C. In some embodiments, the composition is stable for at least about 6 months to about 2 years. In some embodiments, the composition has a pH from about 4.0 to about 7.5. In some embodiments, the composition has a pH from about 4.0 to about 8.5. In some embodiments, the composition has a pH from about 5.0 to about 8.5. In some embodiments, the composition has a pH from about 6.0 to about 7.5. In some embodiments, the composition has a pH from about 7.0 to about 7.5.

In some embodiments, the kit is used for preventing or treating a fungal infection in the pulmonary system of a subject. In some embodiments, the kit is used for preventing a fungal infection in the pulmonary system of a subject. In some embodiments, the kit is used for treating a fungal infection in the pulmonary system of a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 shows the pharmacokinetics of caspofungin in rat plasma when delivered intravenously (dashed line) or via inhalation (solid line) at 2 mg/kg.

FIG. 2 shows the pharmacokinetics of caspofungin in rat plasma when delivered intravenously (dashed line) or via inhalation (solid line) at 2 mg/kg.

FIG. 3 shows the pharmacokinetics of caspofungin in rat lung tissue when delivered intravenously (dashed line) or via inhalation (solid line) at 2 mg/kg.

FIG. 4 shows the pharmacokinetics of caspofungin in rat kidney tissue when delivered intravenously (dashed line) or via inhalation (solid line) at 2 mg/kg.

FIG. 5 shows the pharmacokinetics of caspofungin in rat liver tissue when delivered intravenously (dashed line) or via inhalation (solid line) at 2 mg/kg.

FIG. 6 shows the relative weekly exposure per tissue, Inhaled vs IV, from a single 2 mg/kg dose—a ratio of the 7 day AUC for the inhaled route of delivery compared to the 7 day AUC for intravenous administration.

DETAILED DESCRIPTION OF THE DISCLOSURE

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed. It is intended that the following claims define the scope of the present disclosure and that methods and structures within the scope of these claims and their equivalents be covered thereby.

Unless defined otherwise, all technical and scientific terms used herein have the same meaning as commonly understood by one of skill in the art to which the present disclosure described herein belong. All publications, patents, and patent applications mentioned in this specification are hereby incorporated by reference to the same extent as if each individual publication, patent, or patent application was specifically and individually indicated to be incorporated by reference.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Pulmonary fungal infections are serious infections that usually occur in patients with compromised immune systems and lead to significant mortality and morbidity in such patients. The standard course of treatment requires the administration of antifungal agents intravenously or orally; however, such systemic delivery is associated with numerous side effects, ranging from phlebitis at the infusion site and chills to renal toxicity. The aerosolized delivery of antifungal agents is an attractive alternative for the prevention and treatment of pulmonary fungal lung infections because it allows for the concentrated delivery of the antifungal agent directly to the site of infection with minimal systemic exposure, thus limiting the potential side effects usually associated with intravenous delivery.

The antifungal agent caspofungin is an attractive candidate for aerosolized antifungal therapy. Caspofungin, a macrocyclic lipopeptide, is a member of a class of antifungal agents known as echinocandins, which inhibit the synthesis of glucan in the fungal cell wall through the noncompetitive inhibition of 1,3-β glucan synthesis. Caspofungin has significant activity against fungal infections caused by the *Candida* species, *Aspergillus* species and *Pneumocystis carinii* pneumonia. Furthermore, caspofungin is relatively less toxic than other antifungal agents that are commonly employed for anti-fungal treatment, such as amphotericin B. Despite these advantages, there are no commercially available aerosol formulations of caspofungin for the prevention and/or treatment of antifungal infections.

The commercial formulation of caspofungin is a lyophilized, diacetate salt containing sucrose, mannitol, glacial acetic acid and sodium hydroxide and is reconstituted for intravenous use. Sold by Merck & Company, Inc under the trade name Cancidas®, caspofungin is the first member of the echinocandins to receive US Food and Drug Administration and has been approved for the treatment of invasive aspergillosis in patients who are refractory to or intolerant of other therapies; the empirical therapy for presumed fungal infections in febrile, neutropenic patients; the treatment of candidemia; intra-abdominal abscesses, peritonitis and pleural space infections caused by *candida* infections, and the treatment of esophageal candidiasis.

One challenge in administering caspofungin is that caspofungin is unstable and prone to degradation, especially at room temperature (~25° C.). As such, caspofungin is stored under low temperatures (e.g. 2-8° C.) and is used shortly after reconstitution. There have been various efforts at developing caspofungin formulations with improved stability. The development of the acetate salt of caspofungin, which led to the formulation of Cancidas®, was an improvement over earlier formulations that used the tartrate salt (U.S. Pat. No. 5,952,300). Another example include a formulation that eliminated the acetic acid and sodium hydroxide present in Cancidas® as pH modifiers, wherein the lyophilized and reconstituted formulations demonstrated improved stabilities at 25° C. when compared to the conventional formulations of caspofungin (U.S. Patent Publication 2009/0170753). In another example, a non-reducible sugar, such as trehalose, was used to replace the sucrose and mannitol present in the Cancidas® to provide formulations that have improved storage stability (US Patent Publication 2010/0137197).

Described herein are methods of treating and/or preventing fungal infections in the pulmonary system in a subject in need thereof comprising administering to the subject a composition caspofungin, or a polymorph, pharmaceutically acceptable salt, hydrate, or solvate thereof. In some embodiments, the composition is essentially free of mannitol. In some embodiments, the composition is essentially free of sugar alcohol. In some embodiments, the composition is essentially free of sugar alcohol or sugar. In some embodiments, the composition further comprises an anti-forming agent. The methods described herein allow for the localized and concentrated delivery the caspofungin, or a polymorph, pharmaceutically acceptable salt, hydrate, or solvate thereof directly to the site of infection, the pulmonary tissues, while minimizing the systemic exposure of caspofungin, or a polymorph, pharmaceutically acceptable salt, hydrate, or solvate thereof to other organs.

Echinocandin Tissue Distribution

There are three echinocandins approved for antifungal therapy: caspofungin, micafungin and anidulafungin. All of these compounds are active against a similar range of fungi and are structurally very similar as they are chemically close analogs. Despite their structural similarities it is recognized herein that their distribution and disposition in animals and humans are markedly different and not predictable. For instance, in rat studies, anidulafungin rapidly distributes into tissues to achieve peak concentrations within 30 min and maintains levels above MICs for common pathogens over 72 hours. Furthermore anidulafungin exposure is 9-12 fold higher in tissues susceptible to fungal infection, such as the liver, lung, spleen, kidney, than in plasma (Damle et al., Pharmacokinetics and Tissue Distribution of Anidulafungin in Rats, Antimicrob. Agents Chemo., 2008, 52, 7, p 2673-2676). In contrast, in rat studies, micafungin distributes moderately into the liver, kidney, and lungs, and the tissue concentrations decrease in parallel with micafungin in plasma. Micafungin exposures in the liver, kidney, and lung are 1.6, 3.4, and 2.9 fold higher than that for plasma (Niwa et al., Tissue Distribution after Intravenous Dosing of Micafungin, an Antifungal Drug, to Rats. *Bio Pharm Bull,* 2004, 27, 7, p 1154-1156). It is clear from these studies that tissue/plasma ratios and, thus, the overall tissue penetration for micafungin is considerably less than that observed with anidulafungin.

Caspofungin's tissue distribution has also been examined in non-human species using radiolabeled compound caspofungin (Hadju et al., Preliminary Animal Pharmacokinetics of the Parenteral Antifungal Agent MK-0991 (L-743,872), *Antimicrob. Agents Chemo.,* 1997, 41, 11, p 2339-2344; Stone et. al, Disposition of Caspofungin: Role of Distribution in Determining Pharmacokinetics in Plasma, *Antimicrob. Agents Chemo.*, 2004, 48, 3, p 815-823; and Sandhu et al., Disposition of Caspofungin, a Novel Antifungal Agent, in Mice, Rats, Rabbits, and Monkeys, Antimicrob. *Agents Chemo.*, 2004, 48, 4, p 1272-1280). However, the use of radiolabeled material enables the detection of both parent compound and labeled metabolites, but not the ability to distinguish between them. As such, the reported quantitation of caspofungin may be all caspofungin, all metabolites or an unknown mix of the two with the final case being the most likely scenario. Caspofungin levels in plasma (but not other tissues) were also analyzed for parent compound by Sandhu in 2004. The most complete analysis of caspofungin tissue distribution was published by Stone in 2004 also using radiolabeled material. Comparing Stone's reported radioactive plasma distribution with Sandhu's analysis of the parent compound in plasma it is clear that the parent compound could be 17%, 24% or even 49% of the reported radiolabeled amount. From these studies, it is clear that the tissue distribution of caspofungin has not been determined and is not predictable from comparisons with other echinocandins.

Disclosed herein are tissue distribution studies of caspofungin via intravenous and inhalation administration. The lung retention and tissue distribution characteristics of caspofungin, let alone any approved echinocandin, upon inhaled delivery has not been reported.

Definition of Terms

Unless defined otherwise, all technical and scientific terms used herein have the same meaning as is commonly understood by one of skill in the art to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, are also effective and safe.

As used herein, the phrase "consisting essentially of" is a transitional phrase used in a claim to indicate that the following list of ingredients, parts or process steps must be present in the claimed composition, machine or process, but that the claim is open to unlisted ingredients, parts or process steps that do not materially affect the basic and novel properties of the present disclosure.

The term "prophylaxis" refers to administration of an active pharmaceutical ingredient to a patient with the purpose of reducing the occurrence or recurrence of one or more acute symptoms associated with a disease state or a condition in the patient. In the present context, prophylaxis entails administering caspofungin or the pharmaceutically acceptable salt thereof to a patient via any route of administration disclosed herein. Thus, prophylaxis includes reduction in the occurrence or recurrence rate of a disorder. However, prophylaxis is not intended to include complete prevention of onset of a disease state or a condition in a patient who has not previously been identified as suffering from the disease or the condition.

As used herein, a difference is "significant" if a person skilled in the art would recognize that the difference is probably real. In some embodiments, significance may be determined statistically, in which case two measured parameters may be referred to as statistically significant. In some embodiments, statistical significance may be quantified in terms of a stated confidence interval (CI), e.g., greater than 90%, greater than 95%, greater than 98%, etc. In some embodiments, statistical significance may be quantified in terms of a p value, e.g., less than 0.5, less than 0.1, less than 0.05, etc. The person skilled in the art will recognize these expressions of significance and will know how to apply them appropriately to the specific parameters that are being compared.

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "treat," "treating" or "treatment," and other grammatical equivalents as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "administer," "administering", "administration," and the like, as used herein, refer to the methods that may be used to enable delivery of compounds or compositions to the desired site of biological action. These methods include, but are not limited to inhalation routes, oral routes, intraduodenal routes, parenteral injection (including intravenous, subcutaneous, intraperitoneal, intramuscular, intravascular or infusion), topical and rectal administration.

Those of skill in the art are familiar with administration techniques that can be employed with the compounds and methods described herein. In preferred embodiments, the compounds and compositions described herein are administered via inhalation.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount may differ from one individual to another. An appropriate "effective" amount in any individual case may be determined using techniques, such as a dose escalation study.

The term "acceptable" as used herein, with respect to a formulation, composition or ingredient, means having no persistent detrimental effect on the general health of the individual being treated.

The term "minimum inhibitory concentration" or MIC as used herein, refers to the lowest concentration of an antifungal agent that will inhibit the visible growth of a microorganism after overnight incubation.

The term "minimum effective concentration" or MEC as used herein, refers to the lowest concentration of an antifungal agent that causes abnormal hyphal growth, which is characterized by short abundant branchings.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the present disclosure, or by separately reacting a purified compound in its free base form with a suitable organic or inorganic acid, and isolating the salt thus formed.

Methods of Treatment

Described herein is a method of preventing or treating a fungal infection in the pulmonary system of a subject in need thereof comprising administering to the subject a composition comprising caspofungin, or a polymorph, pharmaceutically acceptable salt, hydrate, or solvate thereof, wherein the composition is essentially free of mannitol. Also described herein is a method of preventing or treating a fungal infection in the pulmonary system of a subject in need thereof comprising administering to the subject a composition comprising caspofungin, or a polymorph, pharmaceutically acceptable salt, hydrate, or solvate thereof, and an anti-foaming agent. Further described herein is a method of preventing or treating a fungal infection in the pulmonary system of a subject in need thereof comprising administering to the subject a composition comprising caspofungin, or a polymorph, pharmaceutically acceptable salt, hydrate, or solvate thereof, and an anti-foaming agent, and wherein the composition is essentially free of mannitol.

Caspofungin

As used herein, caspofungin (CAS 162808-62-0) refers to the compound of the following structure:

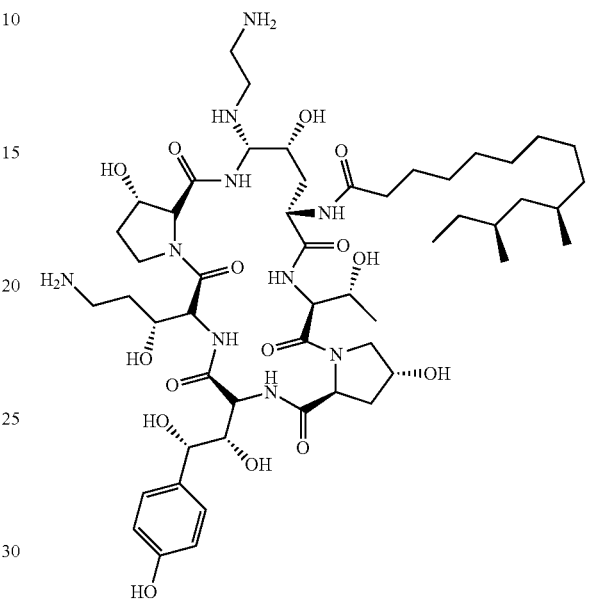

Pharmaceutically Acceptable Salts

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, Handbook of Pharmaceutical Salts: Properties, Selection and Use, Weinheim/Zürich:Wiley-VCH/VHCA, 2002.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the present disclosure, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, in some embodiments, the compounds described herein are prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the present disclosure and their pharmaceutically acceptable acid addition salts.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization. The compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Pharmaceutically acceptable salts of caspofungin include but are not limited to those derived with cations, such as sodium, potassium, aluminum, calcium, lithium, magnesium, and zinc; acids, such as hydrochloric, hydrobromic, phosphoric, sulfuric, maleic, citric, tartaric, succinic, oxalic, malic, glutamic, lactic, propionic and pamoic acids; bases, such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethyl-ammonium hydroxide. Pharmaceutically acceptable salts of caspofungin include the mono-, di-, and tri-acid forms. Also included are pharmaceutically acceptable salts disclosed in U.S. Pat. No. 5,378,804, U.S. Pat. No. 5,936,062, and US 2009/0170753, which are incorporated in reference for their disclosure of such compounds.

In some embodiments, the pharmaceutically acceptable salt of caspofungin is acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate or xylenesulfonate.

Other examples of suitable pharmaceutically acceptable salts of caspofungin include but are not limited to acetates, citrates, tartrates, propionates, succinates, oxalates, malates, maleates, lactates, glutamates, and pamoates. In some embodiments, the pharmaceutically acceptable salt of caspofungin is the acetate. In some embodiments, the pharmaceutically acceptable salt of caspofungin is the propionate. In some embodiments, the pharmaceutically acceptable salt of caspofungin is the lactate.

Solvates and Hydrates

In some embodiments, the compounds described herein exist as solvates. The present disclosure provides for methods of treating diseases by administering such solvates. The present disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The present disclosure provides for methods of treating diseases by administering such polymorphs. The present disclosure further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

In some embodiments, compounds described herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2$H, $^3$H, $^{13}$C, $^{14}$C, $^{15}$N, $^{18}$O, $^{17}$O, $^{35}$S, $^{18}$F, $^{36}$Cl, respectively. Certain isotopically labeled compounds described herein, for example those with isotopes such as deuterium, i.e., $^2$H, can afford certain therapeutic advantages resulting from greater metabolic stability, such as, for example, increased in vivo half-life or reduced dosage requirements. In certain embodiments, caspofungin is isotopically labeled caspofungin, or a polymorph, pharmaceutically acceptable salt, hydrate, or solvate thereof.

Mannitol-Free Caspofungin

It is recognized herein that the aerosolization of the intravenous formulation of caspofungin would not be ideal for inhalation therapy as the mannitol, which is present Cancidas® as a bulking agent that is effective for forming a lyophilized cake, induces cough when inhaled and as well as sugar promotes fungal growth. In some embodiments, the inhalation composition disclosed herein is essentially free of mannitol. In some embodiments, the inhalation composition disclosed herein is essentially free of sugar alcohol. In some embodiments, the inhalation composition disclosed herein is essentially free of sugar alcohol or sugar. Examples of relevant sugar alcohols include but are not limited to glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, and polyglycitol. In some embodiments, the sugar alcohol is glycerol, erythritol, arabitol, xylitol, mannitol, and sorbitol. Examples of relevant sugars include but are not limited to lactose, sucrose, trehalose, dextrose, dextran, and ficoll. In some embodiments, the sugar is sucrose.

Anti-Forming Agents

It is recognized herein that the aerosolization of the intravenous formulation of caspofungin would not be ideal for inhalation therapy as the intravenous formulation of caspofungin foams when nebulized. Such foaming is undesired as it can have an effect on the aerosolization process. In some embodiments, the inhalation compositions described herein comprise an antiforming agent. Antifoaming agents as used herein reduce foaming during processing, which results in coagulation of aqueous dispersions.

In some embodiments the anti-foaming agent is selected from a phospholipid, a fatty acid or derivative thereof, a silicone-based compound, polyethylene glycol copolymer, polypropylene glycol copolymer, and an alkyl polyacrylate. In some embodiments the anti-foaming agent is a phospholipid. Exemplary phospholipids include but are not limited to phosphoglycerides and phosphosphingolipids. Suitable phospholipids also include natural, such as those derived from animal and plant sources, and synthetic phospholipids. Natural phospholipids include, but are not limited to, plasmalogen, cardiolipin, dipalmitoylphosphatidylcholine, glycerophospholipid, glycerophosphoric acid, lecithin, lysophosphatidic acid, phosphatidylcholine, phosphatidylethanolamine, phosphatidylserine, platelet-activating factor, sphingomyelin, ans sphingosyl phosphatide.

In some embodiments, the anti-foaming agent is a fatty acid or derivative thereof. Fatty acids are saturated or unsaturated. Saturated fatty acids include, but are not limited to, lauric acid, myristic acid, palmitic acid, stearic acid, arachidic acid. Unsaturated fatty acids include, but are not limited to, palmitoleic acid, oleic acid, linoleic acid, linolenic acid, arachidonic acid. Suitable fatty acid derivatives include but are not limited to fatty alcohols and fatty esters.

In some embodiments, the anti-foaming agent is a silicone-based compound. Silcone-based compounds include but are not limited to siloxane-based compounds, such as polydimethylsiloxane; simethicone compounds. In some embodiments, the anti-foaming agent is a polyethylene glycol copolymer or a polypropylene glycol copolymer. In some embodiments, the anti-forming agent is an alkyl polyacrylate.

Inhalation Devices

An "inhalation device," as used herein, refers to any device that is capable of administering a drug formulation to the respiratory airways of a patient. Inhalation devices include conventional inhalation devices, such as jet nebulizers, ultrasonic wave nebulizers, high efficiency nebuilizers, heat vaporizers, soft mist inhalers, thermal aerosol inhaler, or electrohydrodynamic-based solution misting inhaler. Nebulizers deliver pharmaceuticals by forming an aerosol which includes droplet sizes that can easily be inhaled. The aerosol can be used by a patient within the bounds of an inhalation therapy, whereby the caspofungin reaches the patient's respiratory tract upon inhalation.

Conventional inhalation devices may be mechanical or electrical, and include, for example, jet nebulizers and ultrasonic nebulizers. Jet nebulizers generally utilize compressors to generate compressed air, which breaks the liquid medication into small breathable droplets, which form an aerosolized (atomized) mist. In some embodiments, when the patient breathes in, a valve at the top opens, which then allows air into the apparatus, thereby speeding up the mist generation; when the patient breathes out, the top valve closes, thereby slowing down the mist generation while simultaneously permitting the patient to breathe out through the opening of a mouthpiece flap. Some nebulizers may provide the aerosol in a continuous mode (e.g., the eFlow from PARI Pharma Starnberg), by a breath enhanced mode (e.g., the PARI LC Plus or Sprint from PARI Starnberg), by breath actuated mode dependent on the breathing pattern of the patient (e.g., the AeroEclipse from Trudell, Canada or the I-Neb from Philips Respironics), or according to given inhalation profile (e.g., the Akita from Activaero, Gmuenden, Germany).

Some conventional inhalation devices are disclosed in U.S. Pat. Nos. 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, each of which is hereby incorporated by reference in its entirety. Commercial conventional inhalation devices include but are not limited to: PARI (Germany) under the trade names PARI LC Plus®, LC Star®, and PARI-Jet®; A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900®; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®, and DeVilbiss (Somerset, Pa.) under the trade name DeVilbiss®; or Trudell, Canada under the trade name AeroEclipse®.

High efficiency nebulizers are inhalation devices that comprise a micro-perforated membrane through which a liquid solution is converted through electrical or mechanical means into aerosol droplets suitable for inhalation. High efficiency nebulizers can deliver a large fraction of a loaded dose to a patient. Commercial high efficiency nebulizers include but are not limited to: PARI (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb®; Omron (Bannockburn, Ill.) under the trade name Micro-Air®; Activaero (Germany) under the trade name Akita®, and AerovectRx (Atlanta, Ga.) under the trade name AerovectRx®.

In some embodiments, the inhalation device selected from a jet nebulizer, ultrasonic wave nebulizer, high efficiency nebulizer, heat vaporizer, soft mist inhaler, thermal aerosol inhaler, or electrohydrodynamic-based solution misting inhaler. In some embodiments, the inhalation device is a jet nebulizer. In some embodiments, the inhalation device is an ultrasonic wave nebulizer. In some embodiments, the inhalation device is a high efficiency nebulizer. In some embodiments, the inhalation device is a heat vaporizer. In some embodiments, the inhalation device is a soft mist inhaler. In some embodiments, the inhalation device is a thermal aerosol inhaler. In some embodiments, the inhalation device is an electrohydrodynamic-based solution misting inhaler.

In some embodiments the caspofungin, or a polymorph, pharmaceutically acceptable salt, hydrate, or solvate thereof is administered with an inhalation device, e.g., jet nebulizers, ultrasonic wave nebulizers, high efficiency nebulizers, heat vaporizers, soft mist inhalers, thermal aerosol inhaler, or electrohydrodynamic-based solution misting inhaler, the methods disclosed herein provide improved efficacy for the treatment or prophylaxis of a fungal infection in the pulmonary system of a subject relative to administration of caspofungin, or a polymorph, pharmaceutically acceptable salt, hydrate, or solvate thereof by a different route of administration, e.g., intravenously, because administration of the caspofungin, or a polymorph, pharmaceutically acceptable salt, hydrate, or solvate thereof with an inhalation device, e.g., jet nebulizers, ultrasonic wave nebulizers, high efficiency nebulizers, heat vaporizers, soft mist inhalers, thermal aerosol inhaler, or electrohydrodynamic-based solution misting inhaler, allows for the attainment of high concentration of caspofungin, or a polymorph, pharmaceutically acceptable salt, hydrate, or solvate thereof in the pulmonary system. In further embodiments, administration of caspofungin, or a polymorph, pharmaceutically acceptable salt, hydrate, or solvate thereof via an inhalation device minimizes systemic toxicities.

Inhalation Therapy

In some embodiments, the administration of the inhalation composition provides a lung tissue concentration of caspofungin or the polymorph, pharmaceutically acceptable salt, hydrate, or solvate thereof that is from about 1-fold to about 100-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 90-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 80-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 70-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 60-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 50-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 40-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 30-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 20-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 10-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 5-fold greater than the concentration in the lung via intravenous administration at the same delivery dose.

In some embodiments, the administration of the inhalation composition provides a lung tissue concentration of caspofungin or the polymorph, pharmaceutically acceptable salt, hydrate, or solvate thereof that is about 1-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 5-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 10-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 20-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 30-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 40-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 50-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 60-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 70-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 80-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 90-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is about 100-fold greater than the concentration in the lung via intravenous administration at the same delivery dose.

In some embodiments, the lung tissue concentration of caspofungin or the polymorph, pharmaceutically acceptable salt, hydrate, or solvate thereof is greater than the concentration in the lung via intravenous administration at the same delivery dose for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the lung tissue concentration of caspofungin or the polymorph, pharmaceutically acceptable salt, hydrate, or solvate thereof is greater than the concentration in the lung via intravenous administration at the same delivery dose for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the lung tissue concentration of caspofungin or the polymorph, pharmaceutically acceptable salt, hydrate, or solvate thereof is greater than the concentration in the lung via intravenous administration at the same delivery dose for 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the lung tissue concentration of caspofungin or the polymorph, pharmaceutically acceptable salt, hydrate, or solvate thereof is greater than the concentration in the lung via intravenous administration at the same delivery dose for 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the lung tissue concentration of caspofungin or the polymorph, pharmaceutically acceptable salt, hydrate, or solvate thereof is greater than the concentration in the lung via intravenous administration at the same delivery dose for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the lung that is from about 1-fold greater to about 1000-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 500-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 200-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 100-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 50-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 20-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 10-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 5-fold greater than the concentration in the liver, kidney, spleen, pancreas or plasma.

In some embodiments, the administration of the inhalation composition provides a concentration of caspofungin or the polymorph, pharmaceutically acceptable salt, hydrate, or solvate thereof in the lung that is about 1-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 2-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 3-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 4-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 5-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 10-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 15-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 20-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 30-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 40-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 50-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 60-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 70-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 80-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 90-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 100-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 110-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 120-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 130-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 140-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 150-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 200-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 300-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 400-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 500-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 600-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 700-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 800-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 900-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 1000-fold greater than the concentration in the liver, kidney, spleen, pancreas or plasma.

In some embodiments, the concentration of caspofungin or the polymorph, pharmaceutically acceptable salt, hydrate, or solvate thereof in the lung is greater than the concentration in the liver, kidney, spleen, pancreas, or plasma for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the liver, kidney, spleen, pancreas, or plasma for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the liver, kidney, spleen, pancreas, or plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the liver, kidney, spleen, pancreas, or plasma for 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the liver, kidney, spleen, pancreas, or plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the lung that is from about 1-fold greater to about 1000-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 500-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 200-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 100-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 50-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 20-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 10-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 5-fold greater than the concentration in the liver.

In some embodiments, the concentration of caspofungin or the polymorph, pharmaceutically acceptable salt, hydrate, or solvate thereof in the lung is greater than the concentration in the liver for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the liver for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the liver for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the liver for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the liver for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the lung that is from about 1-fold greater to about 1000-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 500-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 200-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 100-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 50-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 20-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 10-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 5-fold greater than the concentration in the kidney.

In some embodiments, the concentration of caspofungin or the polymorph, pharmaceutically acceptable salt, hydrate, or solvate thereof in the lung is greater than the concentration in the kidney for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the kidney for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the kidney for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the kidney for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the kidney for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the lung that is from about 1-fold greater to about 1000-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 500-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 200-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 100-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 50-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 20-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 10-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 5-fold greater than the concentration in the spleen.

In some embodiments, the concentration of caspofungin or the polymorph, pharmaceutically acceptable salt, hydrate, or solvate thereof in the lung is greater than the concentration in the spleen for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours.

In some embodiments, the concentration of caspofungin or the polymorph, pharmaceutically acceptable salt, hydrate, or solvate thereof in the lung is greater than the concentration in the spleen for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the spleen for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the spleen for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the spleen for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the lung that is from about 1-fold greater to about 1000-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 500-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 200-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 100-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 50-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 20-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 10-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 5-fold greater than the concentration in the pancreas.

In some embodiments, the concentration of caspofungin or the polymorph, pharmaceutically acceptable salt, hydrate, or solvate thereof in the lung is greater than the concentration in the pancreas for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the pancreas for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the pancreas for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the pancreas for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the pancreas for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the lung that is from about 1-fold greater to about 1000-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 500-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 200-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 100-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 50-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 20-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 10-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 5-fold greater than the concentration in plasma.

In some embodiments, the concentration of caspofungin or the polymorph, pharmaceutically acceptable salt, hydrate, or solvate thereof in the lung is greater than the concentration in the plasma for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in plasma for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the plasma for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the alveolar macrophages that is from about 5-fold greater to about 1000-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 500-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 200-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 150-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 100-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 50-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 20-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 10-fold greater than the concentration in the liver, kidney, spleen, pancreas or plasma.

In some embodiments, the administration of the inhalation composition provides a concentration of caspofungin or the polymorph, pharmaceutically acceptable salt, hydrate, or solvate thereof in the alveolar macrophages that is about 5-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 10-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 20-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 30-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 40-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 50-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 60-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 70-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 80-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 90-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 100-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 150-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 200-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 300-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 400-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 500-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 600-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 700-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 800-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 900-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is about 1000-fold greater than the concentration in the liver, kidney, spleen, pancreas or plasma.

In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the inhalation composition provides a concentration of caspofungin or the polymorph, pharmaceutically acceptable salt, hydrate, or solvate thereof in the alveolar macrophages that is from about 5-fold greater to about 1000-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is from about 5-fold greater to about 500-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is from about 5-fold greater to about 100-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is from about 5-fold greater to about 50-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is from about 5-fold greater to about 20-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is from about 5-fold greater to about 10-fold greater than the concentration in the liver.

In some embodiments, the administration of the inhalation composition provides a concentration of caspofungin or the polymorph, pharmaceutically acceptable salt, hydrate, or solvate thereof in the alveolar macrophages that is about 5-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 10-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 20-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 30-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 40-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 50-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 60-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 70-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 80-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 90-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 100-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 200-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 300-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 400-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 500-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 600-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 700-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 800-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 900-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 1000-fold greater than the concentration in the liver.

In some embodiments, the administration of the inhalation composition provides a concentration of caspofungin or the polymorph, pharmaceutically acceptable salt, hydrate, or solvate thereof in the alveolar macrophages that is from about 5-fold greater to about 1000-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is from about 5-fold greater to about 500-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is from about 5-fold greater to about 100-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is from about 5-fold greater to about 50-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is from about 5-fold greater to about 20-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is from about 5-fold greater to about 10-fold greater than the concentration in the kidney.

In some embodiments, the administration of the inhalation composition provides a concentration of caspofungin or the polymorph, pharmaceutically acceptable salt, hydrate, or solvate thereof in the alveolar macrophages that is about 5-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 10-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 20-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 30-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 40-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 50-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 60-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 70-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 80-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 90-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 100-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 200-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 300-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 400-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 500-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 600-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 700-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 800-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 900-fold greater than the concentration in the kidney. In some embodiments, the administration of the inhalation composition provides a concentration of caspofungin or the polymorph, pharmaceutically acceptable salt, hydrate, or solvate thereof in the alveolar macrophages that is about 1000-fold greater than the concentration in the kidney.

In some embodiments, the administration of the inhalation composition provides a concentration of caspofungin or the polymorph, pharmaceutically acceptable salt, hydrate, or solvate thereof in the alveolar macrophages that is from about 5-fold greater to about 1000-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is from about 5-fold greater to about 500-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is from about 5-fold greater to about 100-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is from about 5-fold greater to about 50-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is from about 5-fold greater to about 20-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is from about 5-fold greater to about 10-fold greater than the concentration in the spleen.

In some embodiments, the administration of the inhalation composition provides a concentration of caspofungin or the polymorph, pharmaceutically acceptable salt, hydrate, or solvate thereof in the alveolar macrophages that is about 5-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 10-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 20-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 30-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 40-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 50-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 60-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 70-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 80-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 90-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 100-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 200-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 300-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 400-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 500-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 600-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 700-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 800-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 900-fold greater than the concentration in the spleen. In some embodiments, the administration of the inhalation composition provides a concentration of caspofungin or the polymorph, pharmaceutically acceptable salt, hydrate, or solvate thereof in the alveolar macrophages that is about 1000-fold greater than the concentration in the spleen.

In some embodiments, the administration of the inhalation composition provides a concentration of caspofungin or the polymorph, pharmaceutically acceptable salt, hydrate, or solvate thereof in the alveolar macrophages that is from about 5-fold greater to about 1000-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is from about 5-fold greater to about 500-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is from about 5-fold greater to about 100-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is from about 5-fold greater to about 50-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is from about 5-fold greater to about 20-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is from about 5-fold greater to about 10-fold greater than the concentration in the pancreas.

In some embodiments, the administration of the inhalation composition provides a concentration of caspofungin or the polymorph, pharmaceutically acceptable salt, hydrate, or solvate thereof in the alveolar macrophages that is about 5-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 10-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 20-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 30-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 40-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 50-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 60-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 70-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 80-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 90-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 100-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 200-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 300-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 400-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 500-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 600-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 700-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 800-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 900-fold greater than the concentration in the pancreas. In some embodiments, the administration of the inhalation composition provides a concentration of caspofungin or the polymorph, pharmaceutically acceptable salt, hydrate, or solvate thereof in the alveolar macrophages that is about 1000-fold greater than the concentration in the pancreas.

In some embodiments, the administration of the inhalation composition provides a concentration of caspofungin or the polymorph, pharmaceutically acceptable salt, hydrate, or solvate thereof in the alveolar macrophages that is from about 5-fold greater to about 1000-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 500-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 100-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 50-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 20-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 10-fold greater than the concentration in plasma.

In some embodiments, the administration of the inhalation composition provides a concentration of caspofungin or the polymorph, pharmaceutically acceptable salt, hydrate, or solvate thereof in the alveolar macrophages that is about 5-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 10-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 20-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 30-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 40-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 50-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 60-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 70-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 80-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 90-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 100-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 200-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 300-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 400-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 500-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 600-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 700-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 800-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 900-fold greater than the concentration in plasma. In some embodiments, the administration of the inhalation composition provides a concentration of caspofungin or the polymorph, pharmaceutically acceptable salt, hydrate, or solvate thereof in the alveolar macrophages that is about 1000-fold greater than the concentration in plasma.

In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 1 hour to about 336 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 3 hours to about 336 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 1 hour after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 3 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 6 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 12 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 24 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 48 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 72 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 96 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 120 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 168 hours after administration. In some embodiments, the concentration of caspofungin or the polymorph, pharmaceutically acceptable salt, hydrate, or solvate thereof in the alveolar macrophages is above the minimum inhibitory concentration (MIC) or the minimum effective concentration (MEC) for about 336 hours after administration.

In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 1 hour to about 336 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 3 hours to about 336 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 1 hour after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 2 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 3 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 6 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 12 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 24 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 48 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 72 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 96 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 120 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 168 hours after administration. In some embodiments, the concentration of caspofungin or the polymorph, pharmaceutically acceptable salt, hydrate, or solvate thereof in the lung is above the minimum inhibitory concentration (MIC) or the minimum effective concentration (MEC) for about 336 hours after administration.

In some embodiments, the minimum inhibitory concentration (MIC) is from about 0.001 µg/mL to about 500 µg/mL. In some embodiments, the minimum inhibitory concentration (MIC) is from about 0.001 µg/mL to about 300 µg/mL. In some embodiments, the minimum inhibitory concentration (MIC) is from about 0.001 µg/mL to about 128 µg/mL. In some embodiments, the minimum inhibitory concentration (MIC) is from about 0.001 µg/mL to about 32 µg/mL. In some embodiments, the minimum inhibitory concentration (MIC) is from about 0.001 µg/mL to about 16 µg/mL.

In some embodiments, the minimum inhibitory concentration (MIC) is from about 0.125 µg/mL to about 500 µg/mL. In some embodiments, the minimum inhibitory concentration (MIC) is from about 0.125 µg/mL to about 300 µg/mL. In some embodiments, the minimum inhibitory concentration (MIC) is from about 0.125 µg/mL to about 128 µg/mL. In some embodiments, the minimum inhibitory concentration (MIC) is from about 0.125 µg/mL to about 32 µg/mL. In some embodiments, the minimum inhibitory concentration (MIC) is from about 0.125 µg/mL to about 16 µg/mL. In some embodiments, the minimum inhibitory concentration (MIC) is from about 0.25 µg/mL to about 16 µg/mL. In some embodiments, the minimum inhibitory concentration (MIC) is from about 0.25 µg/mL to about 32 µg/mL. In some embodiments, the minimum inhibitory concentration (MIC) is from about 0.25 µg/mL to about 128 µg/mL. In some embodiments, the minimum inhibitory concentration (MIC) is from about 16 µg/mL to about 128 µg/mL.

In some embodiments, the minimum inhibitory concentration (MIC) is about 0.001 µg/mL. In some embodiments, the minimum inhibitory concentration (MIC) is about 0.005 µg/mL. In some embodiments, the minimum inhibitory concentration (MIC) is about 0.010 µg/mL. In some embodiments, the minimum inhibitory concentration (MIC) is about 0.015 µg/mL. In some embodiments, the minimum inhibitory concentration (MIC) is about 0.020 µg/mL. In some embodiments, the minimum inhibitory concentration (MIC) is about 0.030 µg/mL. In some embodiments, the minimum inhibitory concentration (MIC) is about 0.040 µg/mL. In some embodiments, the minimum inhibitory concentration (MIC) is about 0.050 µg/mL. In some embodiments, the minimum inhibitory concentration (MIC) is about 0.060 µg/mL. In some embodiments, the minimum inhibitory concentration (MIC) is about 0.070 µg/mL. In some embodiments, the minimum inhibitory concentration (MIC) is about 0.080 µg/mL. In some embodiments, the minimum inhibitory concentration (MIC) is about 0.090 µg/mL. In some embodiments, the minimum inhibitory concentration (MIC) is about 0.100 µg/mL. In some embodiments, the minimum inhibitory concentration (MIC) is about 0.125 µg/mL. In some embodiments, the minimum inhibitory concentration (MIC) is about 0.20 µg/mL. In some embodiments, the minimum inhibitory concentration (MIC) is about 0.25 µg/mL. In some embodiments, the minimum inhibitory concentration (MIC) is about 0.30 µg/mL. In some embodiments, the minimum inhibitory concentration (MIC) is about 0.50 µg/mL. In some embodiments, the minimum inhibitory concentration (MIC) is about 0.75 µg/mL. In some embodiments, the minimum inhibitory concentration (MIC) is about 1.00 µg/mL. In some embodiments, the minimum inhibitory concentration (MIC) is about 1.50 µg/mL. In some embodiments, wherein the minimum inhibitory concentration (MIC) is about 2.00 µg/mL. In some embodiments, wherein the minimum inhibitory concentration (MIC) is about 2.50 µg/mL. In some embodiments, wherein the minimum inhibitory concentration (MIC) is about 3.00 µg/mL. In some embodiments, the minimum inhibitory concentration (MIC) is about 4.00 µg/mL. In some embodiments, the minimum inhibitory concentration (MIC) is about 8.00 µg/mL. In some embodiments, the minimum inhibitory concentration (MIC) is about 10.00 µg/mL. In some embodiments, the minimum inhibitory concentration (MIC) is about 16.00 µg/mL. In some embodiments, the minimum inhibitory concentration (MIC) is about 20.00 µg/mL. In some embodiments, the minimum inhibitory concentration (MIC) is about 30.00 µg/mL. In some embodiments, the minimum inhibitory concentration (MIC) is about 32.00 µg/mL. In some embodiments, the minimum inhibitory concentration (MIC) is about 40.00 µg/mL. In some embodiments, the minimum inhibitory concentration (MIC) is about 60.00 µg/mL. In some embodiments, the minimum inhibitory concentration (MIC) is about 80.00 µg/mL. In some embodiments, the minimum inhibitory concentration (MIC) is about 100.00 µg/mL. In some embodiments, the minimum inhibitory concentration (MIC) is about 120.00 µg/mL. In some embodiments, the minimum inhibitory concentration (MIC) is about 128.00 µg/mL. In some embodiments, the minimum inhibitory concentration (MIC) is about 150.00 µg/mL. In some embodiments, the minimum inhibitory concentration (MIC) is about 200.00 µg/mL. In some embodiments, the minimum inhibitory concentration (MIC) is about 300.00 µg/mL. In some embodiments, the minimum inhibitory concentration (MIC) is about 400.00 µg/mL. In some embodiments, the minimum inhibitory concentration (MIC) is about 500.00 µg/mL.

In some embodiments, the minimum effective concentration (MEC) is from about 0.001 µg/mL to about 500 µg/mL. In some embodiments, the minimum effective concentration (MEC) is from about 0.001 µg/mL to about 300 µg/mL. In some embodiments, the minimum effective concentration (MEC) is from about 0.001 µg/mL to about 128 µg/mL. In some embodiments, the minimum effective concentration (MEC) is from about 0.001 µg/mL to about 32 µg/mL. In some embodiments, the minimum effective concentration (MEC) is from about 0.001 µg/mL to about 16 µg/mL. In some embodiments, the minimum effective concentration (MEC) is from about 0.001 µg/mL to about 1.0 µg/mL. In some embodiments, the minimum effective concentration (MEC) is from about 0.001 µg/mL to about 0.6 µg/mL. In some embodiments, the minimum effective concentration (MEC) is from about 0.001 µg/mL to about 0.3 µg/mL. In some embodiments, the minimum effective concentration (MEC) is from about 0.001 µg/mL to about 0.1 µg/mL. In some embodiments, the minimum effective concentration (MEC) is from about 0.008 µg/mL to about 0.6 µg/mL. In some embodiments, the minimum effective concentration (MEC) is from about 0.008 µg/mL to about 0.3 µg/mL. In some embodiments, the minimum effective concentration (MEC) is from about 0.008 µg/mL to about 0.06 µg/mL.

In some embodiments, minimum effective concentration (MEC) is about 0.001 µg/mL. In some embodiments, the minimum effective concentration (MEC) is about 0.005 µg/mL. In some embodiments, the minimum effective concentration (MEC) is about 0.010 µg/mL. In some embodiments, the minimum effective concentration (MEC) is about 0.015 µg/mL. In some embodiments, the minimum effective concentration (MEC) is about 0.020 µg/mL. In some embodiments, the minimum effective concentration (MEC) is about 0.030 µg/mL. In some embodiments, the minimum effective concentration (MEC) is about 0.040 µg/mL. In some embodiments, the minimum effective concentration (MEC) is about 0.050 µg/mL. In some embodiments, the minimum effective concentration (MEC) is about 0.060 µg/mL. In some embodiments, the minimum effective concentration (MEC) is about 0.070 µg/mL. In some embodiments, the minimum effective concentration (MEC) is about 0.080 µg/mL. In some embodiments, the minimum effective concentration (MEC) is about 0.090 µg/mL. In some embodiments, the minimum effective concentration (MEC) is about 0.100 µg/mL. In some embodiments, the minimum effective concentration (MEC) is about 0.125 µg/mL. In some embodiments, the minimum effective concentration (MEC) is about 0.200 µg/mL. In some embodiments, the minimum effective concentration (MEC) is about 0.250 µg/mL. In some embodiments, the minimum effective concentration (MEC) is about 0.300 µg/mL. In some embodiments, the minimum effective concentration (MEC) is about 0.400 µg/mL. In some embodiments, the minimum effective concentration (MEC) is about 0.500 µg/mL. In some embodiments, the minimum effective concentration (MEC) is about 0.600 µg/mL. In some embodiments, the minimum effective concentration (MEC) is about 0.700 µg/mL. In some embodiments, the minimum effective concentration (MEC) is about 0.75 µg/mL. In some embodiments, the minimum effective concentration (MEC) is about 0.800 µg/mL. In some embodiments, the minimum effective concentration (MEC) is about 0.900 µg/mL. In some embodiments, the minimum effective concentration (MEC) is about 1.000 µg/mL. In some embodiments, the minimum effective concentration (MEC) is about 1.500 µg/mL. In some embodiments, the minimum effective concentration (MEC) is about 2.000 µg/mL. In some embodiments, the minimum effective concentration (MEC) is about 2.500 µg/mL. In some embodiments, the minimum effective concentration (MEC) is about 3.000 µg/mL. In some embodiments, the minimum effective concentration (MEC) is about 4.000 µg/mL. In some embodiments, the minimum effective concentration (MEC) is about 8.000 µg/mL. In some embodiments, the minimum effective concentration (MEC) is about 10.000 µg/mL. In some embodiments, the minimum effective concentration (MEC) is about 16.00 µg/mL. In some embodiments, the minimum effective concentration (MEC) is about 20.00 µg/mL. In some embodiments, the minimum effective concentration (MEC) is about 30.00 µg/mL. In some embodiments, the minimum effective concentration (MEC) is about 32.00 µg/mL. In some embodiments, the minimum effective concentration (MEC) is about 40.00 µg/mL. In some embodiments, the minimum effective concentration (MEC) is about 60.00 µg/mL. In some embodiments, the minimum effective concentration (MEC) is about 80.00 µg/mL. In some embodiments, the minimum effective concentration (MEC) is about 100.00 µg/mL. In some embodiments, the minimum effective concentration (MEC) is about 120.00 µg/mL. In some embodiments, the minimum effective concentration (MEC) is about 128.00 µg/mL. In some embodiments, the minimum effective concentration (MEC) is about 150.00 µg/mL. In some embodiments, the minimum effective concentration (MEC) is about 200.00 µg/mL. In some embodiments, the minimum effective concentration (MEC) is about 300.00 µg/mL. In some embodiments, the minimum effective concentration (MEC) is about 400.00 µg/mL. In some embodiments, the minimum effective concentration (MEC) is about 500.00 µg/mL.

Particle Size

In some embodiments, the inhalation composition is administered by the inhalation device as droplets or particles having a mass median aerodynamic diameter (MMAD) from about 0.5 µm to about 10 µm. In some embodiments, the inhalation composition is administered by the inhalation device as droplets or particles having a mass median aerodynamic diameter (MMAD) from about 0.5 µm to about 5 µm. In some embodiments, the inhalation composition is administered by the inhalation device as droplets or particles having a mass median aerodynamic diameter (MMAD) from about 1 µm to about 10 µm. In some embodiments, the inhalation composition is administered by the inhalation device as droplets or particles having a mass median aerodynamic diameter (MMAD) from about 1 µm to about 5 µm. In some embodiments, the inhalation composition is administered by the inhalation device as droplets or particles having a mass median aerodynamic diameter (MMAD) from about 1 µm to about 4 µm. In some embodiments, the inhalation composition is administered by the inhalation device as droplets or particles having a mass median aerodynamic diameter (MMAD) from about 1 µm to about 3 µm. In some embodiments, the inhalation composition is administered by the inhalation device as droplets or particles having a mass median aerodynamic diameter (MMAD) from about 1 µm to about 3 µm. In some embodiments, the inhalation composition is administered by the inhalation device as droplets or particles having a mass median aerodynamic diameter (MMAD) from about 2 µm to about 3 µm.

In some embodiments, the inhalation composition is administered by the inhalation device as droplets or particles having a mass median aerodynamic diameter (MMAD) of about 0.5 m. In some embodiments, the inhalation composition is administered by the inhalation device as droplets or particles having a mass median aerodynamic diameter (MMAD) of about 1 µm. In some embodiments, the inhalation composition is administered by the inhalation device as droplets or particles having a mass median aerodynamic diameter (MMAD) of about 2 µm. In some embodiments, the inhalation composition is administered by the inhalation device as droplets or particles having a mass median aerodynamic diameter (MMAD) of about 3 µm. In some embodiments, the inhalation composition is administered by the inhalation device as droplets or particles having a mass median aerodynamic diameter (MMAD) of about 4 µm. In some embodiments, the inhalation composition is administered by the inhalation device as droplets or particles having a mass median aerodynamic diameter (MMAD) of about 5 µm. In some embodiments, the inhalation composition is administered by the inhalation device as droplets or particles having a mass median aerodynamic diameter (MMAD) of about 6 µm. In some embodiments, the inhalation composition is administered by the inhalation device as droplets or particles having a mass median aerodynamic diameter (MMAD) of about 7 µm. In some embodiments, the inhalation composition is administered by the inhalation device as droplets or particles having a mass median aerodynamic diameter (MMAD) of about 8 µm. In some embodiments, the inhalation composition is administered by the inhalation device as droplets or particles having a mass median aerodynamic diameter (MMAD) of about 9 µm. In some embodiments, the inhalation composition is administered by the inhalation device as droplets or particles having a mass median aerodynamic diameter (MMAD) of about 10 µm.

In some embodiments, the inhalation composition is administered by the inhalation device as droplets or particles having a GSD (geometric standard deviation) of about 1 to about 3. In some embodiments, the inhalation composition is administered by the inhalation device as droplets or particles having a GSD (geometric standard deviation) of about 2 to about 3.

In some embodiments, the inhalation composition is administered by the inhalation device as droplets or particles having a GSD (geometric standard deviation) is about 1. In some embodiments, the inhalation composition is administered by the inhalation device as droplets or particles having a GSD (geometric standard deviation) is about 2. In some embodiments, the inhalation composition is administered by the inhalation device as droplets or particles having a GSD (geometric standard deviation) is about 3.

Half-Life

In some embodiments, the half-life of the caspofungin, or a polymorph, pharmaceutically acceptable salt, hydrate, or solvate thereof in the lung is about 1 hour to about 100 hours. In some embodiments, the half-life of the caspofungin, or a polymorph, pharmaceutically acceptable salt, hydrate, or solvate thereof in the lung is about 1 hour to about 75 hours. In some embodiments, the half-life of the caspofungin, or a polymorph, pharmaceutically acceptable salt, hydrate, or solvate thereof in the lung is about 1 hour to about 50 hours. In some embodiments, the half-life of the caspofungin, or a polymorph, pharmaceutically acceptable salt, hydrate, or solvate thereof in the lung is about 1 hour to about 20 hours. In some embodiments, the half-life of the caspofungin, or a polymorph, pharmaceutically acceptable salt, hydrate, or solvate thereof in the lung is about 20 hours to about 50 hours. In some embodiments, the half-life of the caspofungin, or a polymorph, pharmaceutically acceptable salt, hydrate, or solvate thereof in the lung is about 30 hours to about 50 hours. In some embodiments, the half-life of the caspofungin, or a polymorph, pharmaceutically acceptable salt, hydrate, or solvate thereof in the lung is about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 50 hours, about 55 hours, about 60 hours, about 65 hours, about 70 hours, about 75 hours, about 80 hours, about 85 hours, about 90 hours, about 95 hours, or about 100 hours.

In some embodiments, the half-life of the caspofungin, or a polymorph, pharmaceutically acceptable salt, hydrate, or solvate thereof in the lung is greater than about 1 hour, greater than about 2 hours, greater than about 3 hours, greater than about 4 hours, greater than about 5 hours, greater than about 6 hours, greater than about 7 hours, greater than about 8 hours, greater than about 9 hours, greater than about 10 hours, greater than about 11 hours, greater than about 12 hours, greater than about 13 hours, greater than about 14 hours, greater than about 15 hours, greater than about 16 hours, greater than about 17 hours, greater than about 18 hours, greater than about 19 hours, greater than about 20 hours, greater than about 21 hours, greater than about 22 hours, greater than about 23 hours, greater than about 24 hours, greater than about 25 hours, greater than about 26 hours, greater than about 27 hours, greater than about 28 hours, greater than about 29 hours, greater than about 30 hours, greater than about 31 hours, greater than about 32 hours, greater than about 33 hours, greater than about 34 hours, greater than about 35 hours, greater than about 36 hours, greater than about 37 hours, greater than about 38 hours, greater than about 39 hours, greater than about 40 hours, greater than about 41 hours, greater than about 42 hours, greater than about 43 hours, greater than about 44 hours, greater than about 45 hours, greater than about 50 hours, greater than about 55 hours, greater than about 60 hours, greater than about 65 hours, greater than about 70 hours, greater than about 75 hours, greater than about 80 hours, greater than about 85 hours, greater than about 90 hours, greater than about 95 hours, or greater than about 100 hours.

In some embodiments, the half-life of the caspofungin, or a polymorph, pharmaceutically acceptable salt, hydrate, or solvate thereof in the lung is less than about 1 hour, less than about 2 hours, less than about 3 hours, less than about 4 hours, less than about 5 hours, less than about 6 hours, less than about 7 hours, less than about 8 hours, less than about 9 hours, less than about 10 hours, less than about 11 hours, less than about 12 hours, less than about 13 hours, less than about 14 hours, less than about 15 hours, less than about 16 hours, less than about 17 hours, less than about 18 hours, less than about 19 hours, less than about 20 hours, less than about 21 hours, less than about 22 hours, less than about 23 hours, less than about 24 hours, less than about 25 hours, less than about 26 hours, less than about 27 hours, less than about 28 hours, less than about 29 hours, less than about 30 hours, less than about 31 hours, less than about 32 hours, less than about 33 hours, less than about 34 hours, less than about 35 hours, less than about 36 hours, less than about 37 hours, less than about 38 hours, less than about 39 hours, less than about 40 hours, less than about 41 hours, less than about 42 hours, less than about 43 hours, less than about 44 hours, less than about 45 hours, less than about 50 hours, less than about 55 hours, less than about 60 hours, less than about 65 hours, less than about 70 hours, less than about 75 hours, less than about 80 hours, less than about 85 hours, less than about 90 hours, less than about 95 hours, or less than about 100 hours.

Stability

In some embodiments, the inhalation composition is stable from at about −20° C. to about 25° C. In some embodiments, the inhalation composition is stable from at about 5° C. to about 25° C. In some embodiments, the inhalation composition is stable at about −20° C. In some embodiments, the inhalation composition is stable at about −15° C. In some embodiments, the inhalation composition is stable at about −10° C. In some embodiments, the inhalation composition is stable at about −5° C. In some embodiments, the inhalation composition is stable at about 0° C. In some embodiments, the inhalation composition is stable at about 5° C. In some embodiments, the inhalation composition is stable at about 6° C. In some embodiments, the inhalation composition is stable at about 7° C. In some embodiments, the inhalation composition is stable at about 8° C. In some embodiments, the inhalation composition is stable at about 9° C. In some embodiments, the inhalation composition is stable at about 10° C. In some embodiments, the inhalation composition is stable at about 11° C. In some embodiments, the inhalation composition is stable at about 12° C. In some embodiments, the inhalation composition is stable at about 13° C. In some embodiments, the inhalation composition is stable at about 14° C. In some embodiments, the inhalation composition is stable at about 15° C. In some embodiments, the inhalation composition is stable at about 16° C. In some embodiments, the inhalation composition is stable at about 17° C. In some embodiments, the inhalation composition is stable at about 18° C. In some embodiments, the inhalation composition is stable at about 19° C. In some embodiments, the inhalation composition is stable at about 20° C. In some embodiments, the inhalation composition is stable at about 21° C. In some embodiments, the inhalation composition is stable at about 22° C. In some embodiments, the inhalation composition is stable at about 23° C. In some embodiments, the inhalation composition is stable at about 24° C. In some embodiments, the inhalation composition is stable at about 25° C.

In some embodiments, the inhalation compositions disclosed herein are stable for at least about 6 months to about 2 years. In some embodiments, the inhalation composition disclosed herein is stable for at least about 6 months. In some embodiments, the inhalation composition disclosed herein is stable for at least about 7 months. In some embodiments, the inhalation composition disclosed herein is for at least about 8 months. In some embodiments, the inhalation composition disclosed herein is stable for at least about 9 months. In some embodiments, the inhalation composition disclosed herein is stable for at least about 10 months. In some embodiments, the inhalation composition disclosed herein is stable for at least about 11 months. In some embodiments, the inhalation composition is stable for at least about 12 months. In some embodiments, the inhalation composition disclosed herein is stable for at least about 13 months. In some embodiments, the inhalation composition disclosed herein is stable for at least about 14 months. In some embodiments, the inhalation composition disclosed herein is stable for at least about 15 months. In some embodiments, the inhalation composition disclosed herein is stable for at least about 16 months. In some embodiments, the inhalation composition disclosed herein is stable for at least about 17 months. In some embodiments, the inhalation composition is stable for at least about 18 months. In some embodiments, the inhalation composition disclosed herein is stable for at least about 19 months. In some embodiments, the inhalation composition disclosed herein is stable for at least about 20 months. In some embodiments, the inhalation composition disclosed herein is stable for at least about 21 months. In some embodiments, the inhalation composition disclosed herein is stable for at least about 22 months. In some embodiments, the inhalation composition disclosed herein is stable for at least about 23 months. In some embodiments, the inhalation composition disclosed herein is stable for at least about 24 months (2 years).

pH

In some embodiments, the inhalation composition has a pH from about 4.0 to about 8.5. In some embodiments, the inhalation composition has a pH from about 4.0 to about 7.5. In some embodiments, the inhalation composition has a pH from about 5.0 to about 8.5. In some embodiments, the inhalation composition has a pH from about 6.0 to about 7.5. In some embodiments, the inhalation composition has a pH from about 7.0 to about 7.5. In some embodiments, the inhalation composition has a pH of about 4.0. In some embodiments, the inhalation composition has a pH of about 4.5. In some embodiments, the inhalation composition has a pH of about 5.0. In some embodiments, the inhalation composition has a pH of about 5.5. In some embodiments, the inhalation composition has a pH of about 6.0. In some embodiments, the inhalation composition has a pH of about 6.5. In some embodiments, the inhalation composition has a pH of about 7.0. In some embodiments, the inhalation composition has a pH of about 7.5. In some embodiments, the inhalation composition has a pH of about 8.0. In some embodiments, the inhalation composition has a pH of about 8.5.

Pulmonary Infections

Disclosed herein is a method for the prevention or treatment of a pulmonary infection in the pulmonary system. In some embodiments, the method is for treating a fungal infection caused by *Candida* sp., and/or by *Aspergillus* sp., and/or by *Pneumocystis jirovecii*. In some embodiments, the method is for treating an infection caused by *Candida* sp., and/or by *Aspergillus* sp. In some embodiments, the method is for treating a fungal infection caused by *Candida albicans, Candida tropicalis, Candida krusei, Candida glabrata, Candida guilliermondii,* or *Candida parapsilosis*. In some embodiments, the method is for treating a fungal infection caused by *Candida albicans, Candida tropicalis, Candida krusei,* or *Candida glabrata*. In some embodiments, the method for treating a fungal infection caused by *Aspergillus fumigatus, Aspergillus flavus, Aspergillus niger,* or *Aspergillus terreus*. In some embodiments, the method for treating a fungal infection is caused by *Aspergillus fumigatus, Aspergillus flavus,* or *Aspergillus niger*.

In some embodiments, the method is for preventing a fungal infection caused by *Candida* sp., and/or by *Aspergillus* sp., and/or by *Pneumocystis jirovecii*. In some embodiments, the method is for preventing an infection caused by *Candida* sp., and/or by *Aspergillus* sp. In some embodiments, the method is for treating a fungal infection caused by *Candida albicans, Candida tropicalis, Candida krusei, Candida glabrata, Candida guilliermondii,* or *Candida parapsilosis*. In some embodiments, the method is for preventing a fungal infection caused by *Candida albicans, Candida tropicalis, Candida krusei,* or *Candida glabrata*. In some embodiments, the method for treating a fungal infection caused by *Aspergillus fumigatus, Aspergillus flavus, Aspergillus niger,* or *Aspergillus terreus*. In some embodiments, the method for preventing a fungal infection is caused by *Aspergillus fumigatus, Aspergillus flavus,* or *Aspergillus niger*.

In some embodiments, the subject is immunocompromised. In some embodiments, the subject is a transplant recipient or a subject undergoing cancer chemotherapy. In some embodiments, the subject is a transplant recipient. In some embodiments, the subject is undergoing cancer chemotherapy. In some embodiments, the subject is a recipient of a hematopoietic stem-cell transplant, bone marrow transplant, lung transplant, liver transplant, heart transplant, kidney transplant, pancreas transplant or a combination thereof. In some embodiments, the subject is a recipient of a hematopoietic stem-cell transplant. In some embodiments, the subject is a recipient of a bone marrow transplant. In some embodiments, the subject is a recipient of a lung transplant. In some embodiments, the subject is a recipient of a liver transplant. In some embodiments, the subject is a recipient of a heart transplant. In some embodiments, the subject is a recipient of a kidney transplant. In some embodiments, the subject is a recipient of a pancreas transplant.

Kits

Provided herein is a kit comprising a composition suitable for administration via inhalation, wherein the composition comprises caspofungin, or a polymorph, pharmaceutically acceptable salt, hydrate, or solvate thereof, and wherein the composition is essentially free of mannitol; and an inhalation device.

In some embodiments, the kit is used for preventing or treating a fungal infection in the pulmonary system of a subject. In some embodiments, the kit is used for preventing a fungal infection in the pulmonary system of a subject. In some embodiments, the kit is used for treating a fungal infection in the pulmonary system of a subject.

In some embodiments, the kit is for treating a fungal infection caused by *Candida* sp., and/or by *Aspergillus* sp., and/or by *Pneumocystis jirovecii*. In some embodiments, the kit is for treating an infection caused by *Candida* sp., and/or by *Aspergillus* sp. In some embodiments, the kit is for treating a fungal infection caused by *Candida albicans,*

*Candida tropicalis, Candida krusei, Candida glabrata, Candida guilliermondii,* or *Candida parapsilosis.* In some embodiments, the kit is for treating a fungal infection caused by *Candida albicans, Candida tropicalis, Candida krusei,* or *Candida glabrata.* In some embodiments, the kit for treating a fungal infection caused by *Aspergillus fumigatus, Aspergillus flavus, Aspergillus niger,* or *Aspergillus terreus.* In some embodiments, the kit is for treating a fungal infection caused by *Aspergillus fumigatus, Aspergillus flavus,* or *Aspergillus niger.*

In some embodiments, kit is for preventing a fungal infection caused by *Candida* sp., and/or by *Aspergillus* sp., and/or by *Pneumocystis jirovecii.* In some embodiments, the kit is for preventing an infection caused by *Candida* sp., and/or by *Aspergillus* sp. In some embodiments, the kit is for treating a fungal infection caused by *Candida albicans, Candida tropicalis, Candida krusei, Candida glabrata, Candida guilliermondii,* or *Candida parapsilosis.* In some embodiments, the kit is for preventing a fungal infection caused by *Candida albicans, Candida tropicalis, Candida krusei,* or *Candida glabrata.* In some embodiments, the kit for treating a fungal infection caused by *Aspergillus fumigatus, Aspergillus flavus, Aspergillus niger,* or *Aspergillus terreus.* In some embodiments, the kit is for preventing a fungal infection caused by *Aspergillus fumigatus, Aspergillus flavus,* or *Aspergillus niger.*

In some embodiments, the composition disclosed herein is essentially free of mannitol. In some embodiments, the composition disclosed herein is essentially free of sugar alcohol. In some embodiments, the composition disclosed herein is essentially free of sugar alcohol or sugar.

In some embodiments, the administration of the composition provides a lung tissue concentration of caspofungin or the polymorph, pharmaceutically acceptable salt, hydrate, or solvate thereof that is from about 1-fold to about 100-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 90-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 80-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 70-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 60-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is from about 1-fold to about 50-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 40-fold greater than the concentration in the lung via intravenous administration at the same delivery dose. In some embodiments, the administration of the inhalation composition provides a lung tissue concentration of caspofungin or the polymorph, pharmaceutically acceptable salt, hydrate, or solvate thereof that is from about 1-fold to about 30-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is from about 1-fold to about 20-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is from about 1-fold to about 10-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is from about 1-fold to about 5-fold greater than the concentration in the lung via intravenous administration at the same delivery dose.

In some embodiments, the administration of the composition provides a lung tissue concentration of caspofungin or the polymorph, pharmaceutically acceptable salt, hydrate, or solvate thereof that is about 1-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 5-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 10-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 20-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 30-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 40-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 50-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 60-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 70-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 80-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 90-fold greater than the concentration in the lung via intravenous administration at the same delivery dose. In some embodiments, the administration of the composition provides a lung tissue concentration of caspofungin or the polymorph, pharmaceutically acceptable salt, hydrate, or solvate thereof that is about 100-fold greater than the concentration in the lung via intravenous administration at the same delivery dose.

In some embodiments, the lung tissue concentration of caspofungin or the polymorph, pharmaceutically acceptable salt, hydrate, or solvate thereof is greater than the concentration in the lung via intravenous administration at the same delivery dose for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the lung tissue concentration of caspofungin or the polymorph, pharmaceutically acceptable salt, hydrate, or solvate thereof is greater than the concentration in the lung via intravenous administration at the same delivery dose for 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the lung tissue concentration of caspofungin or the polymorph, pharmaceutically acceptable salt, hydrate, or solvate thereof is greater than the concentration in the lung via intravenous administration at the same delivery dose for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the lung tissue concentration of caspofungin or the polymorph, pharmaceutically acceptable salt, hydrate, or solvate thereof is greater than the concentration in the lung via intravenous administration at the same delivery dose for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the lung tissue concentration of caspofungin or the polymorph, pharmaceutically acceptable salt, hydrate, or solvate thereof is greater than the concentration in the lung via intravenous administration at the same delivery dose for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin or the polymorph, pharmaceutically acceptable salt, hydrate, or solvate thereof in the lung that is from about 1-fold greater to about 1000-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is from about 1-fold greater to about 500-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is from about 1-fold greater to about 200-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is from about 1-fold greater to about 100-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is from about 1-fold greater to about 50-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is from about 1-fold greater to about 20-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is from about 1-fold greater to about 10-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is from about 1-fold greater to about 5-fold greater than the concentration in the liver, kidney, spleen, pancreas or plasma.

In some embodiments, the administration of the composition provides a concentration of caspofungin or the polymorph, pharmaceutically acceptable salt, hydrate, or solvate thereof in the lung that is about 1-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 2-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 3-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 4-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 5-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 10-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 15-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 20-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 30-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 40-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 50-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 60-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 70-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 80-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 90-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 100-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 110-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 120-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 130-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 140-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the lung that is about 150-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 200-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 300-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 400-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 500-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 600-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 700-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 800-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 900-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the lung that is about 1000-fold greater than the concentration in the liver, kidney, spleen, pancreas or plasma.

In some embodiments, the concentration of caspofungin or the polymorph, pharmaceutically acceptable salt, hydrate, or solvate thereof in the lung is greater than the concentration in the liver, kidney, spleen, pancreas, or plasma for about 0.5 hour to about 336 hours, 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the liver, kidney, spleen, pancreas, or plasma for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the liver, kidney, spleen, pancreas, or plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the liver, kidney, spleen, pancreas, or plasma for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the liver, kidney, spleen, pancreas, or plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin or the polymorph, pharmaceutically acceptable salt, hydrate, or solvate thereof in the lung that is from about 1-fold greater to about 1000-fold greater than the concentration in the liver. In some embodiments, the administration of the composition provides a concentration of caspofungin or the polymorph, pharmaceutically acceptable salt, hydrate, or solvate thereof in the lung that is from about 1-fold greater to about 500-fold greater than the concentration in the liver. In some embodiments, the administration of the composition provides a concentration of caspofungin or the polymorph, pharmaceutically acceptable salt, hydrate, or solvate thereof in the lung that is from about 1-fold greater to about 200-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the liver. In some embodiments, the administration of the composition provides a concentration of caspofungin or the polymorph, pharmaceutically acceptable salt, hydrate, or solvate thereof in the lung that is from about 1-fold greater to about 100-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the liver. In some embodiments, the administration of the composition provides a concentration of caspofungin or the polymorph, pharmaceutically acceptable salt, hydrate, or solvate thereof in the lung that is from about 1-fold greater to about 50-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the liver. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the liver. In some embodiments, the administration of the composition provides a concentration of caspofungin or the polymorph, pharmaceutically acceptable salt, hydrate, or solvate thereof in the lung that is from about 1-fold greater to about 20-fold greater than the concentration in the liver. In some embodiments, the administration of the composition provides a concentration of caspofungin or the polymorph, pharmaceutically acceptable salt, hydrate, or solvate thereof in the lung that is from about 1-fold greater to about 10-fold greater than the concentration in the liver. In some embodiments, the administration of the composition provides a concentration of caspofungin or the polymorph, pharmaceutically acceptable salt, hydrate, or solvate thereof in the lung that is from about 1-fold greater to about 5-fold greater than the concentration in the liver.

In some embodiments, the concentration of caspofungin or the polymorph, pharmaceutically acceptable salt, hydrate, or solvate thereof in the lung is greater than the concentration in the liver for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the liver for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the liver for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the liver for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the liver for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin or the polymorph, pharmaceutically acceptable salt, hydrate, or solvate thereof in the lung that is from about 1-fold greater to about 1000-fold greater than the concentration in the kidney. In some embodiments, the administration of the composition provides a concentration of caspofungin or the polymorph, pharmaceutically acceptable salt, hydrate, or solvate thereof in the lung that is from about 1-fold greater to about 500-fold greater than the concentration in the kidney. In some embodiments, the administration of the composition provides a concentration of caspofungin or the polymorph, pharmaceutically acceptable salt, hydrate, or solvate thereof in the lung that is from about 1-fold greater to about 200-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the kidney. In some embodiments, the administration of the composition provides a concentration of caspofungin or the polymorph, pharmaceutically acceptable salt, hydrate, or solvate thereof in the lung that is from about 1-fold greater to about 100-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the kidney. In some embodiments, the administration of the composition provides a concentration of caspofungin or the polymorph, pharmaceutically acceptable salt, hydrate, or solvate thereof in the lung that is from about 1-fold greater to about 50-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the kidney. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the kidney. In some embodiments, the administration of the composition provides a concentration of caspofungin or the polymorph, pharmaceutically acceptable salt, hydrate, or solvate thereof in the lung that is from about 1-fold greater to about 20-fold greater than the concentration in the kidney. In some embodiments, the administration of the composition provides a concentration of caspofungin or the polymorph, pharmaceutically acceptable salt, hydrate, or solvate thereof in the lung that is from about 1-fold greater to about 10-fold greater than the concentration in the kidney. In some embodiments, the administration of the composition provides a concentration of caspofungin or the polymorph, pharmaceutically acceptable salt, hydrate, or solvate thereof in the lung that is from about 1-fold greater to about 5-fold greater than the concentration in the kidney.

In some embodiments, the concentration of caspofungin or the polymorph, pharmaceutically acceptable salt, hydrate, or solvate thereof in the lung is greater than the concentration in the kidney for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the kidney for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the kidney for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the kidney for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the kidney for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin or the polymorph, pharmaceutically acceptable salt, hydrate, or solvate thereof in the lung that is from about 1-fold greater to about 1000-fold greater than the concentration in the spleen. In some embodiments, the administration of the composition provides a concentration of caspofungin or the polymorph, pharmaceutically acceptable salt, hydrate, or solvate thereof in the lung that is from about 1-fold greater to about 500-fold greater than the concentration in the spleen. In some embodiments, the administration of the composition provides a concentration of caspofungin or the polymorph, pharmaceutically acceptable salt, hydrate, or solvate thereof in the lung that is from about 1-fold greater to about 200-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the spleen. In some embodiments, the administration of the composition provides a concentration of caspofungin or the polymorph, pharmaceutically acceptable salt, hydrate, or solvate thereof in the lung that is from about 1-fold greater to about 100-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the spleen. In some embodiments, the administration of the composition provides a concentration of caspofungin or the polymorph, pharmaceutically acceptable salt, hydrate, or solvate thereof in the lung that is from about 1-fold greater to about 50-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the spleen. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the spleen. In some embodiments, the administration of the composition provides a concentration of caspofungin or the polymorph, pharmaceutically acceptable salt, hydrate, or solvate thereof in the lung that is from about 1-fold greater to about 20-fold greater than the concentration in the spleen. In some embodiments, the administration of the composition provides a concentration of caspofungin or the polymorph, pharmaceutically acceptable salt, hydrate, or solvate thereof in the lung that is from about 1-fold greater to about 10-fold greater than the concentration in the spleen. In some embodiments, the administration of the composition provides a concentration of caspofungin or the polymorph, pharmaceutically acceptable salt, hydrate, or solvate thereof in the lung that is from about 1-fold greater to about 5-fold greater than the concentration in the spleen.

In some embodiments, the concentration of caspofungin or the polymorph, pharmaceutically acceptable salt, hydrate, or solvate thereof in the lung is greater than the concentration in the spleen for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the spleen for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the spleen for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the spleen for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the spleen for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours. In some embodiments, the administration of composition provides a concentration of caspofungin or the polymorph, pharmaceutically acceptable salt, hydrate, or solvate thereof in the lung that is from about 1-fold greater to about 1000-fold greater than the concentration in the pancreas. In some embodiments, the administration of the composition provides a concentration of caspofungin or the polymorph, pharmaceutically acceptable salt, hydrate, or solvate thereof in the lung that is from about 1-fold greater to about 500-fold greater than the concentration in the pancreas. In some embodiments, the administration of the composition provides a concentration of caspofungin or the polymorph, pharmaceutically acceptable salt, hydrate, or solvate thereof in the lung that is from about 1-fold greater to about 200-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in the pancreas. In some embodiments, the administration of the composition provides a concentration of caspofungin or the polymorph, pharmaceutically acceptable salt, hydrate, or solvate thereof in the lung that is from about 1-fold greater to about 100-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in the pancreas. In some embodiments, the administration of the composition provides a concentration of caspofungin or the polymorph, pharmaceutically acceptable salt, hydrate, or solvate thereof in the lung that is from about 1-fold greater to about 50-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in the pancreas. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in the pancreas. In some embodiments, the administration of the composition provides a concentration of caspofungin or the polymorph, pharmaceutically acceptable salt, hydrate, or solvate thereof in the lung that is from about 1-fold greater to about 20-fold greater than the concentration in the pancreas. In some embodiments, the administration of the composition provides a concentration of caspofungin or the polymorph, pharmaceutically acceptable salt, hydrate, or solvate thereof in the lung that is from about 1-fold greater to about 10-fold greater than the concentration in the pancreas. In some embodiments, the administration of the composition provides a concentration of caspofungin or the polymorph, pharmaceutically acceptable salt, hydrate, or solvate thereof in the lung that is from about 1-fold greater to about 5-fold greater than the concentration in the pancreas.

In some embodiments, the concentration of caspofungin or the polymorph, pharmaceutically acceptable salt, hydrate, or solvate thereof in the lung is greater than the concentration in the pancreas for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in the pancreas for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the pancreas for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the pancreas for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the pancreas for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin or the polymorph, pharmaceutically acceptable salt, hydrate, or solvate thereof in the lung that is from about 1-fold greater to about 1000-fold greater than the concentration in plasma. In some embodiments, the administration of the composition provides a concentration of caspofungin or the polymorph, pharmaceutically acceptable salt, hydrate, or solvate thereof in the lung that is from about 1-fold greater to about 500-fold greater than the concentration in plasma. In some embodiments, the administration of the composition provides a concentration of caspofungin or the polymorph, pharmaceutically acceptable salt, hydrate, or solvate thereof in the lung that is from about 1-fold greater to about 200-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 150-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 120-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 110-fold greater than the concentration in plasma. In some embodiments, the administration of the composition provides a concentration of caspofungin or the polymorph, pharmaceutically acceptable salt, hydrate, or solvate thereof in the lung that is from about 1-fold greater to about 100-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 90-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 80-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 70-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 60-fold greater than the concentration in plasma. In some embodiments, the administration of the composition provides a concentration of caspofungin or the polymorph, pharmaceutically acceptable salt, hydrate, or solvate thereof in the lung that is from about 1-fold greater to about 50-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 40-fold greater than the concentration in plasma. In some embodiments, the administration of the inhalation composition provides a concentration of caspofungin or the polymorph, pharmaceutically acceptable salt, hydrate, or solvate thereof in the lung that is from about 1-fold greater to about 30-fold greater than the concentration in plasma. In some embodiments, the administration of the composition provides a concentration of caspofungin or the polymorph, pharmaceutically acceptable salt, hydrate, or solvate thereof in the lung that is from about 1-fold greater to about 20-fold greater than the concentration in plasma. In some embodiments, the administration of the composition provides a concentration of caspofungin or the polymorph, pharmaceutically acceptable salt, hydrate, or solvate thereof in the lung that is from about 1-fold greater to about 10-fold greater than the concentration in plasma. In some embodiments, the administration of the composition provides a concentration of caspofungin or the polymorph, pharmaceutically acceptable salt, hydrate, or solvate thereof in the lung that is from about 1-fold greater to about 5-fold greater than the concentration in plasma.

In some embodiments, the concentration of caspofungin or the polymorph, pharmaceutically acceptable salt, hydrate, or solvate thereof in the lung is greater than the concentration in the plasma for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the lung is greater than the concentration in plasma for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the lung is greater than the concentration in the plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the lung is greater than the concentration in the plasma for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the lung is greater than the concentration in the plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin or the polymorph, pharmaceutically acceptable salt, hydrate, or solvate thereof in the alveolar macrophages that is from about 5-fold greater to about 1000-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is from about 5-fold greater to about 500-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 200-fold greater than the concentration in the liver, kidney, spleen, pancreas or plasma. In some embodiments, the administration of the inhalation composition provides a concentration of caspofungin or the polymorph, pharmaceutically acceptable salt, hydrate, or solvate thereof in the alveolar macrophages that is from about 5-fold greater to about 150-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is from about 5-fold greater to about 100-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is from about 5-fold greater to about 50-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is from about 5-fold greater to about 20-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is from about 5-fold greater to about 10-fold greater than the concentration in the liver, kidney, spleen, pancreas or plasma.

In some embodiments, the administration of the composition provides a concentration of caspofungin or the polymorph, pharmaceutically acceptable salt, hydrate, or solvate thereof in the alveolar macrophages that is about 5-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 10-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 20-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 30-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 40-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 50-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 60-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 70-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 80-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 90-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 100-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 150-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 200-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 300-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 400-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 500-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 600-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 700-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 800-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 900-fold greater than the concentration in the liver, kidney, spleen, pancreas or plasma. In some embodiments, the administration of the composition provides a concentration of caspofungin or the polymorph, pharmaceutically acceptable salt, hydrate, or solvate thereof in the alveolar macrophages that is about 1000-fold greater than the concentration in the liver, kidney, spleen, pancreas or plasma.

In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin or the polymorph, pharmaceutically acceptable salt, hydrate, or solvate thereof in the alveolar macrophages is greater than the concentration in the liver, kidney, spleen, pancreas, or plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin or the polymorph, pharmaceutically acceptable salt, hydrate, or solvate thereof in the alveolar macrophages that is from about 5-fold greater to about 1000-fold greater than the concentration in the liver. In some embodiments, the administration of the composition provides a concentration of caspofungin or the polymorph, pharmaceutically acceptable salt, hydrate, or solvate thereof in the alveolar macrophages that is from about 5-fold greater to about 500-fold greater than the concentration in the liver. In some embodiments, the administration of the composition provides a concentration of caspofungin or the polymorph, pharmaceutically acceptable salt, hydrate, or solvate thereof in the alveolar macrophages that is from about 5-fold greater to about 100-fold greater than the concentration in the liver. In some embodiments, the administration of the composition provides a concentration of caspofungin or the polymorph, pharmaceutically acceptable salt, hydrate, or solvate thereof in the alveolar macrophages that is from about 5-fold greater to about 50-fold greater than the concentration in the liver. In some embodiments, the administration of the composition provides a concentration of caspofungin or the polymorph, pharmaceutically acceptable salt, hydrate, or solvate thereof in the alveolar macrophages that is from about 5-fold greater to about 20-fold greater than the concentration in the liver. In some embodiments, the administration of the composition provides a concentration of caspofungin or the polymorph, pharmaceutically acceptable salt, hydrate, or solvate thereof in the alveolar macrophages that is from about 5-fold greater to about 10-fold greater than the concentration in the liver.

In some embodiments, the administration of the composition provides a concentration of caspofungin or the polymorph, pharmaceutically acceptable salt, hydrate, or solvate thereof in the alveolar macrophages that is about 5-fold greater than the concentration in the liver. In some embodiments, the administration of the composition provides a concentration of caspofungin or the polymorph, pharmaceutically acceptable salt, hydrate, or solvate thereof in the alveolar macrophages that is about 10-fold greater than the concentration in the liver. In some embodiments, the administration of the composition provides a concentration of caspofungin or the polymorph, pharmaceutically acceptable salt, hydrate, or solvate thereof in the alveolar macrophages that is about 20-fold greater than the concentration in the liver. In some embodiments, the administration of the composition provides a concentration of caspofungin or the polymorph, pharmaceutically acceptable salt, hydrate, or solvate thereof in the alveolar macrophages that is about 30-fold greater than the concentration in the liver. In some embodiments, the administration of the inhalation composition provides a concentration of caspofungin or the polymorph, pharmaceutically acceptable salt, hydrate, or solvate thereof in the alveolar macrophages that is about 40-fold greater than the concentration in the liver. In some embodiments, the administration of the composition provides a concentration of caspofungin or the polymorph, pharmaceutically acceptable salt, hydrate, or solvate thereof in the alveolar macrophages that is about 50-fold greater than the concentration in the liver.

In some embodiments, the administration of the composition provides a concentration of caspofungin or the polymorph, pharmaceutically acceptable salt, hydrate, or solvate thereof in the alveolar macrophages that is about 60-fold greater than the concentration in the liver. In some embodiments, the administration of the composition provides a concentration of caspofungin or the polymorph, pharmaceutically acceptable salt, hydrate, or solvate thereof in the alveolar macrophages that is about 70-fold greater than the concentration in the liver. In some embodiments, the administration of the composition provides a concentration of caspofungin or the polymorph, pharmaceutically acceptable salt, hydrate, or solvate thereof in the alveolar macrophages that is about 80-fold greater than the concentration in the liver. In some embodiments, the administration of the composition provides a concentration of caspofungin or the polymorph, pharmaceutically acceptable salt, hydrate, or solvate thereof in the alveolar macrophages that is about 90-fold greater than the concentration in the liver. In some embodiments, the administration of the composition provides a concentration of caspofungin or the polymorph, pharmaceutically acceptable salt, hydrate, or solvate thereof in the alveolar macrophages that is about 100-fold greater than the concentration in the liver. In some embodiments, the administration of the composition provides a concentration of caspofungin or the polymorph, pharmaceutically acceptable salt, hydrate, or solvate thereof in the alveolar macrophages that is about 200-fold greater than the concentration in the liver. In some embodiments, the administration of the composition provides a concentration of caspofungin or the polymorph, pharmaceutically acceptable salt, hydrate, or solvate thereof in the alveolar macrophages that is about 300-fold greater than the concentration in the liver. In some embodiments, the administration of the composition provides a concentration of caspofungin or the polymorph, pharmaceutically acceptable salt, hydrate, or solvate thereof in the alveolar macrophages that is about 400-fold greater than the concentration in the liver. In some embodiments, the administration of the composition provides a concentration of caspofungin or the polymorph, pharmaceutically acceptable salt, hydrate, or solvate thereof in the alveolar macrophages that is about 500-fold greater than the concentration in the liver. In some embodiments, the administration of the composition provides a concentration of caspofungin or the polymorph, pharmaceutically acceptable salt, hydrate, or solvate thereof in the alveolar macrophages that is about 600-fold greater than the concentration in the liver. In some embodiments, the administration of the composition provides a concentration of caspofungin or the polymorph, pharmaceutically acceptable salt, hydrate, or solvate thereof in the alveolar macrophages that is about 700-fold greater than the concentration in the liver. In some embodiments, the administration of the composition provides a concentration of caspofungin or the polymorph, pharmaceutically acceptable salt, hydrate, or solvate thereof in the alveolar macrophages that is about 800-fold greater than the concentration in the liver. In some embodiments, the administration of the composition provides a concentration of caspofungin or the polymorph, pharmaceutically acceptable salt, hydrate, or solvate thereof in the alveolar macrophages that is about 900-fold greater than the concentration in the liver. In some embodiments, the administration of the composition provides a concentration of caspofungin or the polymorph, pharmaceutically acceptable salt, hydrate, or solvate thereof in the alveolar macrophages that is about 1000-fold greater than the concentration in the liver.

In some embodiments, the administration of the composition provides a concentration of caspofungin or the polymorph, pharmaceutically acceptable salt, hydrate, or solvate thereof in the alveolar macrophages that is from about 5-fold greater to about 1000-fold greater than the concentration in the kidney. In some embodiments, the administration of the composition provides a concentration of caspofungin or the polymorph, pharmaceutically acceptable salt, hydrate, or solvate thereof in the alveolar macrophages that is from about 5-fold greater to about 500-fold greater than the concentration in the kidney. In some embodiments, the administration of the composition provides a concentration of caspofungin or the polymorph, pharmaceutically acceptable salt, hydrate, or solvate thereof in the alveolar macrophages that is from about 5-fold greater to about 100-fold greater than the concentration in the kidney. In some embodiments, the administration of the composition provides a concentration of caspofungin or the polymorph, pharmaceutically acceptable salt, hydrate, or solvate thereof in the alveolar macrophages that is from about 5-fold greater to about 50-fold greater than the concentration in the kidney. In some embodiments, the administration of the composition provides a concentration of caspofungin or the polymorph, pharmaceutically acceptable salt, hydrate, or solvate thereof in the alveolar macrophages that is from about 5-fold greater to about 20-fold greater than the concentration in the kidney. In some embodiments, the administration of the composition provides a concentration of caspofungin or the polymorph, pharmaceutically acceptable salt, hydrate, or solvate thereof in the alveolar macrophages that is from about 5-fold greater to about 10-fold greater than the concentration in the kidney.

In some embodiments, the administration of the composition provides a concentration of caspofungin or the polymorph, pharmaceutically acceptable salt, hydrate, or solvate thereof in the alveolar macrophages that is about 5-fold greater than the concentration in the kidney. In some embodiments, the administration of the composition provides a concentration of caspofungin or the polymorph, pharmaceutically acceptable salt, hydrate, or solvate thereof in the alveolar macrophages that is about 10-fold greater than the concentration in the kidney. In some embodiments, the administration of the composition provides a concentration of caspofungin or the polymorph, pharmaceutically acceptable salt, hydrate, or solvate thereof in the alveolar macrophages that is about 20-fold greater than the concentration in the kidney. In some embodiments, the administration of the composition provides a concentration of caspofungin or the polymorph, pharmaceutically acceptable salt, hydrate, or solvate thereof in the alveolar macrophages that is about 30-fold greater than the concentration in the kidney. In some embodiments, the administration of the composition provides a concentration of caspofungin or the polymorph, pharmaceutically acceptable salt, hydrate, or solvate thereof in the alveolar macrophages that is about 40-fold greater than the concentration in the kidney. In some embodiments, the administration of the composition provides a concentration of caspofungin or the polymorph, pharmaceutically acceptable salt, hydrate, or solvate thereof in the alveolar macrophages that is about 50-fold greater than the concentration in the kidney. In some embodiments, the administration of the composition provides a concentration of caspofungin or the polymorph, pharmaceutically acceptable salt, hydrate, or solvate thereof in the alveolar macrophages that is about 60-fold greater than the concentration in the kidney. In some embodiments, the administration of the composition provides a concentration of caspofungin or the polymorph, pharmaceutically acceptable salt, hydrate, or solvate thereof in the alveolar macrophages that is about 70-fold greater than the concentration in the kidney. In some embodiments, the administration of the composition provides a concentration of caspofungin or the polymorph, pharmaceutically acceptable salt, hydrate, or solvate thereof in the alveolar macrophages that is about 80-fold greater than the concentration in the kidney. In some embodiments, the administration of the composition provides a concentration of caspofungin or the polymorph, pharmaceutically acceptable salt, hydrate, or solvate thereof in the alveolar macrophages that is about 90-fold greater than the concentration in the kidney. In some embodiments, the administration of the composition provides a concentration of caspofungin or the polymorph, pharmaceutically acceptable salt, hydrate, or solvate thereof in the alveolar macrophages that is about 100-fold greater than the concentration in the kidney. In some embodiments, the administration of the composition provides a concentration of caspofungin or the polymorph, pharmaceutically acceptable salt, hydrate, or solvate thereof in the alveolar macrophages that is about 200-fold greater than the concentration in the kidney. In some embodiments, the administration of the composition provides a concentration of caspofungin or the polymorph, pharmaceutically acceptable salt, hydrate, or solvate thereof in the alveolar macrophages that is about 300-fold greater than the concentration in the kidney. In some embodiments, the administration of the composition provides a concentration of caspofungin or the polymorph, pharmaceutically acceptable salt, hydrate, or solvate thereof in the alveolar macrophages that is about 400-fold greater than the concentration in the kidney. In some embodiments, the administration of the composition provides a concentration of caspofungin or the polymorph, pharmaceutically acceptable salt, hydrate, or solvate thereof in the alveolar macrophages that is about 500-fold greater than the concentration in the kidney. In some embodiments, the administration of the composition provides a concentration of caspofungin or the polymorph, pharmaceutically acceptable salt, hydrate, or solvate thereof in the alveolar macrophages that is about 600-fold greater than the concentration in the kidney. In some embodiments, the administration of the composition provides a concentration of caspofungin or the polymorph, pharmaceutically acceptable salt, hydrate, or solvate thereof in the alveolar macrophages that is about 700-fold greater than the concentration in the kidney. In some embodiments, the administration of the composition provides a concentration of caspofungin or the polymorph, pharmaceutically acceptable salt, hydrate, or solvate thereof in the alveolar macrophages that is about 800-fold greater than the concentration in the kidney. In some embodiments, the administration of the composition provides a concentration of caspofungin or the polymorph, pharmaceutically acceptable salt, hydrate, or solvate thereof in the alveolar macrophages that is about 900-fold greater than the concentration in the kidney. In some embodiments, the administration of the composition provides a concentration of caspofungin or the polymorph, pharmaceutically acceptable salt, hydrate, or solvate thereof in the alveolar macrophages that is about 1000-fold greater than the concentration in the kidney.

In some embodiments, the administration of the composition provides a concentration of caspofungin or the polymorph, pharmaceutically acceptable salt, hydrate, or solvate thereof in the alveolar macrophages that is from about 5-fold greater to about 1000-fold greater than the concentration in the spleen. In some embodiments, the administration of the composition provides a concentration of caspofungin or the polymorph, pharmaceutically acceptable salt, hydrate, or solvate thereof in the alveolar macrophages that is from about 5-fold greater to about 500-fold greater than the concentration in the spleen. In some embodiments, the administration of the composition provides a concentration of caspofungin or the polymorph, pharmaceutically acceptable salt, hydrate, or solvate thereof in the alveolar macrophages that is from about 5-fold greater to about 100-fold greater than the concentration in the spleen. In some embodiments, the administration of the composition provides a concentration of caspofungin or the polymorph, pharmaceutically acceptable salt, hydrate, or solvate thereof in the alveolar macrophages that is from about 5-fold greater to about 50-fold greater than the concentration in the spleen. In some embodiments, the administration of the composition provides a concentration of caspofungin or the polymorph, pharmaceutically acceptable salt, hydrate, or solvate thereof in the alveolar macrophages that is from about 5-fold greater to about 20-fold greater than the concentration in the spleen. In some embodiments, the administration of the composition provides a concentration of caspofungin or the polymorph, pharmaceutically acceptable salt, hydrate, or solvate thereof in the alveolar macrophages that is from about 5-fold greater to about 10-fold greater than the concentration in the spleen.

In some embodiments, the administration of the composition provides a concentration of caspofungin or the polymorph, pharmaceutically acceptable salt, hydrate, or solvate thereof in the alveolar macrophages that is about 5-fold greater than the concentration in the spleen. In some embodiments, the administration of the composition provides a concentration of caspofungin or the polymorph, pharmaceutically acceptable salt, hydrate, or solvate thereof in the alveolar macrophages that is about 10-fold greater than the concentration in the spleen. In some embodiments, the administration of the composition provides a concentration of caspofungin or the polymorph, pharmaceutically acceptable salt, hydrate, or solvate thereof in the alveolar macrophages that is about 20-fold greater than the concentration in the spleen. In some embodiments, the administration of the composition provides a concentration of caspofungin or the polymorph, pharmaceutically acceptable salt, hydrate, or solvate thereof in the alveolar macrophages that is about 30-fold greater than the concentration in the spleen. In some embodiments, the administration of the composition provides a concentration of caspofungin or the polymorph, pharmaceutically acceptable salt, hydrate, or solvate thereof in the alveolar macrophages that is about 40-fold greater than the concentration in the spleen. In some embodiments, the administration of the composition provides a concentration of caspofungin or the polymorph, pharmaceutically acceptable salt, hydrate, or solvate thereof in the alveolar macrophages that is about 50-fold greater than the concentration in the spleen. In some embodiments, the administration of the composition provides a concentration of caspofungin or the polymorph, pharmaceutically acceptable salt, hydrate, or solvate thereof in the alveolar macrophages that is about 60-fold greater than the concentration in the spleen. In some embodiments, the administration of the composition provides a concentration of caspofungin or the polymorph, pharmaceutically acceptable salt, hydrate, or solvate thereof in the alveolar macrophages that is about 70-fold greater than the concentration in the spleen. In some embodiments, the administration of the composition provides a concentration of caspofungin or the polymorph, pharmaceutically acceptable salt, hydrate, or solvate thereof in the alveolar macrophages that is about 80-fold greater than the concentration in the spleen. In some embodiments, the administration of the composition provides a concentration of caspofungin or the polymorph, pharmaceutically acceptable salt, hydrate, or solvate thereof in the alveolar macrophages that is about 90-fold greater than the concentration in the spleen. In some embodiments, the administration of the composition provides a concentration of caspofungin or the polymorph, pharmaceutically acceptable salt, hydrate, or solvate thereof in the alveolar macrophages that is about 100-fold greater than the concentration in the spleen. In some embodiments, the administration of the composition provides a concentration of caspofungin or the polymorph, pharmaceutically acceptable salt, hydrate, or solvate thereof in the alveolar macrophages that is about 200-fold greater than the concentration in the spleen. In some embodiments, the administration of the composition provides a concentration of caspofungin or the polymorph, pharmaceutically acceptable salt, hydrate, or solvate thereof in the alveolar macrophages that is about 300-fold greater than the concentration in the spleen. In some embodiments, the administration of the composition provides a concentration of caspofungin or the polymorph, pharmaceutically acceptable salt, hydrate, or solvate thereof in the alveolar macrophages that is about 400-fold greater than the concentration in the spleen. In some embodiments, the administration of the composition provides a concentration of caspofungin or the polymorph, pharmaceutically acceptable salt, hydrate, or solvate thereof in the alveolar macrophages that is about 500-fold greater than the concentration in the spleen. In some embodiments, the administration of the composition provides a concentration of caspofungin or the polymorph, pharmaceutically acceptable salt, hydrate, or solvate thereof in the alveolar macrophages that is about 600-fold greater than the concentration in the spleen. In some embodiments, the administration of the composition provides a concentration of caspofungin or the polymorph, pharmaceutically acceptable salt, hydrate, or solvate thereof in the alveolar macrophages that is about 700-fold greater than the concentration in the spleen. In some embodiments, the administration of the composition provides a concentration of caspofungin or the polymorph, pharmaceutically acceptable salt, hydrate, or solvate thereof in the alveolar macrophages that is about 800-fold greater than the concentration in the spleen. In some embodiments, the administration of the composition provides a concentration of caspofungin or the polymorph, pharmaceutically acceptable salt, hydrate, or solvate thereof in the alveolar macrophages that is about 900-fold greater than the concentration in the spleen. In some embodiments, the administration of the composition provides a concentration of caspofungin or the polymorph, pharmaceutically acceptable salt, hydrate, or solvate thereof in the alveolar macrophages that is about 1000-fold greater than the concentration in the spleen.

In some embodiments, the administration of the composition provides a concentration of caspofungin or the polymorph, pharmaceutically acceptable salt, hydrate, or solvate thereof in the alveolar macrophages that is from about 5-fold greater to about 1000-fold greater than the concentration in the pancreas. In some embodiments, the administration of the composition provides a concentration of caspofungin or the polymorph, pharmaceutically acceptable salt, hydrate, or solvate thereof in the alveolar macrophages that is from about 5-fold greater to about 500-fold greater than the concentration in the pancreas. In some embodiments, the administration of the composition provides a concentration of caspofungin or the polymorph, pharmaceutically acceptable salt, hydrate, or solvate thereof in the alveolar macrophages that is from about 5-fold greater to about 100-fold greater than the concentration in the pancreas. In some embodiments, the administration of the composition provides a concentration of caspofungin or the polymorph, pharmaceutically acceptable salt, hydrate, or solvate thereof in the alveolar macrophages that is from about 5-fold greater to about 50-fold greater than the concentration in the pancreas. In some embodiments, the administration of the composition provides a concentration of caspofungin or the polymorph, pharmaceutically acceptable salt, hydrate, or solvate thereof in the alveolar macrophages that is from about 5-fold greater to about 20-fold greater than the concentration in the pancreas. In some embodiments, the administration of the composition provides a concentration of caspofungin or the polymorph, pharmaceutically acceptable salt, hydrate, or solvate thereof in the alveolar macrophages that is from about 5-fold greater to about 10-fold greater than the concentration in the pancreas.

In some embodiments, the administration of the composition provides a concentration of caspofungin or the polymorph, pharmaceutically acceptable salt, hydrate, or solvate thereof in the alveolar macrophages that is about 5-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 10-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 20-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 30-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 40-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 50-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 60-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 70-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 80-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 90-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 100-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 200-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 300-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 400-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 500-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 600-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 700-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 800-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 900-fold greater than the concentration in the pancreas. In some embodiments, the administration of the composition provides a concentration of caspofungin or the polymorph, pharmaceutically acceptable salt, hydrate, or solvate thereof in the alveolar macrophages that is about 1000-fold greater than the concentration in the pancreas.

In some embodiments, the administration of the composition provides a concentration of caspofungin or the polymorph, pharmaceutically acceptable salt, hydrate, or solvate thereof in the alveolar macrophages that is from about 5-fold greater to about 1000-fold greater than the concentration in plasma. In some embodiments, the administration of the composition provides a concentration of caspofungin or the polymorph, pharmaceutically acceptable salt, hydrate, or solvate thereof in the alveolar macrophages that is from about 5-fold greater to about 500-fold greater than the concentration in plasma. In some embodiments, the administration of the composition provides a concentration of caspofungin or the polymorph, pharmaceutically acceptable salt, hydrate, or solvate thereof in the alveolar macrophages that is from about 5-fold greater to about 100-fold greater than the concentration in plasma. In some embodiments, the administration of the composition provides a concentration of caspofungin or the polymorph, pharmaceutically acceptable salt, hydrate, or solvate thereof in the alveolar macrophages that is from about 5-fold greater to about 50-fold greater than the concentration in plasma. In some embodiments, the administration of the composition provides a concentration of caspofungin or the polymorph, pharmaceutically acceptable salt, hydrate, or solvate thereof in the alveolar macrophages that is from about 5-fold greater to about 20-fold greater than the concentration in plasma. In some embodiments, the administration of the composition provides a concentration of caspofungin or the polymorph, pharmaceutically acceptable salt, hydrate, or solvate thereof in the alveolar macrophages that is from about 5-fold greater to about 10-fold greater than the concentration in plasma.

In some embodiments, the administration of the composition provides a concentration of caspofungin or the polymorph, pharmaceutically acceptable salt, hydrate, or solvate thereof in the alveolar macrophages that is about 5-fold greater than the concentration in plasma. In some embodiments, the administration of the composition provides a concentration of caspofungin or the polymorph, pharmaceutically acceptable salt, hydrate, or solvate thereof in the alveolar macrophages that is about 10-fold greater than the concentration in plasma. In some embodiments, the administration of the composition provides a concentration of caspofungin or the polymorph, pharmaceutically acceptable salt, hydrate, or solvate thereof in the alveolar macrophages is about 20-fold greater than the concentration in plasma. In some embodiments, the administration of the composition provides a concentration of caspofungin or the polymorph, pharmaceutically acceptable salt, hydrate, or solvate thereof in the alveolar macrophages that is about 30-fold greater than the concentration in plasma. In some embodiments, the administration of the composition provides a concentration of caspofungin or the polymorph, pharmaceutically acceptable salt, hydrate, or solvate thereof in the alveolar macrophages that is about 40-fold greater than the concentration in plasma.

In some embodiments, the administration of the composition provides a concentration of caspofungin or the polymorph, pharmaceutically acceptable salt, hydrate, or solvate thereof in the alveolar macrophages that is about 50-fold greater than the concentration in plasma. In some embodiments, the administration of the composition provides a concentration of caspofungin or the polymorph, pharmaceutically acceptable salt, hydrate, or solvate thereof in the alveolar macrophages that is about 60-fold greater than the concentration in plasma. In some embodiments, the administration of the composition provides a concentration of caspofungin or the polymorph, pharmaceutically acceptable salt, hydrate, or solvate thereof in the alveolar macrophages that is about 70-fold greater than the concentration in plasma. In some embodiments, the administration of the composition provides a concentration of caspofungin or the polymorph, pharmaceutically acceptable salt, hydrate, or solvate thereof in the alveolar macrophages is about 80-fold greater than the concentration in plasma. In some embodiments, the administration of the composition provides a concentration of caspofungin or the polymorph, pharmaceutically acceptable salt, hydrate, or solvate thereof in the alveolar macrophages that is about 90-fold greater than the concentration in plasma. In some embodiments, the administration of the composition provides a concentration of caspofungin or the polymorph, pharmaceutically acceptable salt, hydrate, or solvate thereof in the alveolar macrophages that is about 100-fold greater than the concentration in plasma. In some embodiments, the administration of the composition provides a concentration of caspofungin or the polymorph, pharmaceutically acceptable salt, hydrate, or solvate thereof in the alveolar macrophages that is about 200-fold greater than the concentration in plasma. In some embodiments, the administration of the composition provides a concentration of caspofungin or the polymorph, pharmaceutically acceptable salt, hydrate, or solvate thereof in the alveolar macrophages that is about 300-fold greater than the concentration in plasma. In some embodiments, the administration of the composition provides a concentration of caspofungin or the polymorph, pharmaceutically acceptable salt, hydrate, or solvate thereof in the alveolar macrophages that is about 400-fold greater than the concentration in plasma. In some embodiments, the administration of the composition provides a concentration of caspofungin or the polymorph, pharmaceutically acceptable salt, hydrate, or solvate thereof in the alveolar macrophages that is about 500-fold greater than the concentration in plasma. In some embodiments, the administration of the composition provides a concentration of caspofungin or the polymorph, pharmaceutically acceptable salt, hydrate, or solvate thereof in the alveolar macrophages that is about 600-fold greater than the concentration in plasma. In some embodiments, the administration of the composition provides a concentration of caspofungin or the polymorph, pharmaceutically acceptable salt, hydrate, or solvate thereof in the alveolar macrophages that is about 700-fold greater than the concentration in plasma. In some embodiments, the administration of the composition provides a concentration of caspofungin or the polymorph, pharmaceutically acceptable salt, hydrate, or solvate thereof in the alveolar macrophages that is about 800-fold greater than the concentration in plasma. In some embodiments, the administration of the composition provides a concentration of caspofungin or the polymorph, pharmaceutically acceptable salt, hydrate, or solvate thereof in the alveolar macrophages that is about 900-fold greater than the concentration in plasma. In some embodiments, the administration of the composition provides a concentration of caspofungin or the polymorph, pharmaceutically acceptable salt, hydrate, or solvate thereof in the alveolar macrophages that is about 1000-fold greater than the concentration in plasma.

In some embodiments, the inhalation composition is administered by the inhalation device as droplets or particles having a mass median aerodynamic diameter (MMAD) from about 0.5 µm to about 10 µm. In some embodiments, the inhalation composition is administered by the inhalation device as droplets or particles having a mass median aerodynamic diameter (MMAD) from about 0.5 µm to about 5 µm. In some embodiments, the composition is administered by the device as droplets or particles having a mass median aerodynamic diameter (MMAD) from about 1 µm to about 10 µm. In some embodiments, the composition is administered by the inhalation device as droplets or particles having a mass median aerodynamic diameter (MMAD) from about 1 µm to about 5 µm. In some embodiments, the inhalation composition is administered by the inhalation device as droplets or particles having a mass median aerodynamic diameter (MMAD) from about 1 µm to about 4 µm. In some embodiments, the inhalation composition is administered by the inhalation device as droplets or particles having a mass median aerodynamic diameter (MMAD) from about 1 µm to about 3 µm. In some embodiments, the composition is administered by the inhalation device as droplets or particles having a mass median aerodynamic diameter (MMAD) from about 2 µm to about 3 µm.

In some embodiments, the inhalation composition is administered by the inhalation device as droplets or particles having a mass median aerodynamic diameter (MMAD) of about 0.5 µm. In some embodiments, the composition is administered by the inhalation device as droplets or particles having a mass median aerodynamic diameter (MMAD) of about 1 µm. In some embodiments, the composition is administered by the inhalation device as droplets or particles having a mass median aerodynamic diameter (MMAD) of about 2 µm. In some embodiments, the composition is administered by the inhalation device as droplets or particles having a mass median aerodynamic diameter (MMAD) of about 3 µm. In some embodiments, the composition is administered by the inhalation device as droplets or particles having a mass median aerodynamic diameter (MMAD) of about 4 µm. In some embodiments, the composition is administered by the inhalation device as droplets or particles having a mass median aerodynamic diameter (MMAD) of about 5 µm. In some embodiments, the composition is administered by the inhalation device as droplets or particles having a mass median aerodynamic diameter (MMAD) of about 6 µm. In some embodiments, the composition is administered by the inhalation device as droplets or particles having a mass median aerodynamic diameter (MMAD) of about 7 µm. In some embodiments, the composition is administered by the inhalation device as droplets or particles having a mass median aerodynamic diameter (MMAD) of about 8 µm. In some embodiments, the composition is administered by the inhalation device as droplets or particles having a mass median aerodynamic diameter (MMAD) of about 9 µm. In some embodiments, the composition is administered by the inhalation device as droplets or particles having a mass median aerodynamic diameter (MMAD) of about 10 µm.

In some embodiments, the inhalation composition is administered by the inhalation device as droplets or particles having a GSD (geometric standard deviation) of about 1 to about 3. In some embodiments, the inhalation composition is administered by the inhalation device as droplets or particles having a GSD (geometric standard deviation) of about 2 to about 3.

In some embodiments, the inhalation composition is administered by the inhalation device as droplets or particles having a GSD (geometric standard deviation) is about 1. In some embodiments, the inhalation composition is administered by the inhalation device as droplets or particles having a GSD (geometric standard deviation) is about 2. In some embodiments, the inhalation composition is administered by the inhalation device as droplets or particles having a GSD (geometric standard deviation) is about 3.

In some embodiments, the half-life of the caspofungin, or a polymorph, pharmaceutically acceptable salt, hydrate, or solvate thereof in the lung is about 1 hour to about 100 hours. In some embodiments, the half-life of the caspofungin, or a polymorph, pharmaceutically acceptable salt, hydrate, or solvate thereof in the lung is about 1 hour to about 75 hours. In some embodiments, the half-life of the caspofungin, or a polymorph, pharmaceutically acceptable salt, hydrate, or solvate thereof in the lung is about 1 hour to about 50 hours. In some embodiments, the half-life of the caspofungin, or a polymorph, pharmaceutically acceptable salt, hydrate, or solvate thereof in the lung is about 1 hour to about 20 hours. In some embodiments, the half-life of the caspofungin, or a polymorph, pharmaceutically acceptable salt, hydrate, or solvate thereof in the lung is about 20 hours to about 50 hours. In some embodiments, the half-life of the caspofungin, or a polymorph, pharmaceutically acceptable salt, hydrate, or solvate thereof in the lung is about 30 hours to about 50 hours. In some embodiments, the half-life of the caspofungin, or a polymorph, pharmaceutically acceptable salt, hydrate, or solvate thereof in the lung is about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 50 hours, about 55 hours, about 60 hours, about 65 hours, about 70 hours, about 75 hours, about 80 hours, about 85 hours, about 90 hours, about 95 hours, or about 100 hours.

In some embodiments, the half-life of the caspofungin, or a polymorph, pharmaceutically acceptable salt, hydrate, or solvate thereof in the lung is greater than about 1 hour, greater than about 2 hours, greater than about 3 hours, greater than about 4 hours, greater than about 5 hours, greater than about 6 hours, greater than about 7 hours, greater than about 8 hours, greater than about 9 hours, greater than about 10 hours, greater than about 11 hours, greater than about 12 hours, greater than about 13 hours, greater than about 14 hours, greater than about 15 hours, greater than about 16 hours, greater than about 17 hours, greater than about 18 hours, greater than about 19 hours, greater than about 20 hours, greater than about 21 hours, greater than about 22 hours, greater than about 23 hours, greater than about 24 hours, greater than about 25 hours, greater than about 26 hours, greater than about 27 hours, greater than about 28 hours, greater than about 29 hours, greater than about 30 hours, greater than about 31 hours, greater than about 32 hours, greater than about 33 hours, greater than about 34 hours, greater than about 35 hours, greater than about 36 hours, greater than about 37 hours, greater than about 38 hours, greater than about 39 hours, greater than about 40 hours, greater than about 41 hours, greater than about 42 hours, greater than about 43 hours, greater than about 44 hours, greater than about 45 hours, greater than about 50 hours, greater than about 55 hours, greater than about 60 hours, greater than about 65 hours, greater than about 70 hours, greater than about 75 hours, greater than about 80 hours, greater than about 85 hours, greater than about 90 hours, greater than about 95 hours, or greater than about 100 hours.

In some embodiments, the half-life of the caspofungin, or a polymorph, pharmaceutically acceptable salt, hydrate, or solvate thereof in the lung is less than about 1 hour, less than about 2 hours, less than about 3 hours, less than about 4 hours, less than about 5 hours, less than about 6 hours, less than about 7 hours, less than about 8 hours, less than about 9 hours, less than about 10 hours, less than about 11 hours, less than about 12 hours, less than about 13 hours, less than about 14 hours, less than about 15 hours, less than about 16 hours, less than about 17 hours, less than about 18 hours, less than about 19 hours, less than about 20 hours, less than about 21 hours, less than about 22 hours, less than about 23 hours, less than about 24 hours, less than about 25 hours, less than about 26 hours, less than about 27 hours, less than about 28 hours, less than about 29 hours, less than about 30 hours, less than about 31 hours, less than about 32 hours, less than about 33 hours, less than about 34 hours, less than about 35 hours, less than about 36 hours, less than about 37 hours, less than about 38 hours, less than about 39 hours, less than about 40 hours, less than about 41 hours, less than about 42 hours, less than about 43 hours, less than about 44 hours, less than about 45 hours, less than about 50 hours, less than about 55 hours, less than about 60 hours, less than about 65 hours, less than about 70 hours, less than about 75 hours, less than about 80 hours, less than about 85 hours, less than about 90 hours, less than about 95 hours, or less than about 100 hours.

In some embodiments, the inhalation composition is stable at about −20° C. to about 25° C. In some embodiments, the composition is stable from at about 5° C. to about 25° C. In some embodiments, the composition is stable at about −20° C. In some embodiments, the composition is stable at about −15° C. In some embodiments, the composition is stable at about −10° C. In some embodiments, the composition is stable at about −5° C. In some embodiments, the composition is stable at about 0° C. In some embodiments, the composition is stable at about 5° C. In some embodiments, the composition is stable at about 6° C. In some embodiments, the composition is stable at about 7° C. In some embodiments, the composition is stable at about 8° C. In some embodiments, the composition is stable at about 9° C. In some embodiments, the composition is stable at about 10° C. In some embodiments, the composition is stable at about 11° C. In some embodiments, the composition is stable at about 12° C. In some embodiments, the composition is stable at about 13° C. In some embodiments, the composition is stable at about 14° C. In some embodiments, the composition is stable at about 15° C. In some embodiments, the composition is stable at about 16° C. In some embodiments, the composition is stable at about 17° C. In some embodiments, the composition is stable at about 18° C. In some embodiments, the composition is stable at about 19° C. In some embodiments, the composition is stable at about 20° C. In some embodiments, the composition is stable at about 21° C. In some embodiments, the composition is stable at about 22° C. In some embodiments, the composition is stable at about 23° C. In some embodiments, the composition is stable at about 24° C. In some embodiments, the composition is stable at about 25° C.

In some embodiments, the compositions disclosed herein are stable for at least about 6 months to about 2 years. In some embodiments, the composition disclosed herein is stable for at least about 6 months. In some embodiments, the composition disclosed herein is stable for at least about 7 months. In some embodiments, the composition disclosed herein is stable for at least about 8 months. In some embodiments, the composition disclosed herein is stable for at least about 9 months. In some embodiments, the composition disclosed herein is stable for at least about 10 months. In some embodiments, the composition disclosed herein is stable for at least about 11 months. In some embodiments, the composition disclosed herein is stable for at least about 12 months. In some embodiments, the composition disclosed herein is stable for at least about 13 months. In some embodiments, the composition disclosed herein is stable for at least about 14 months. In some embodiments, the composition disclosed herein is stable for at least about 15 months. In some embodiments, the composition disclosed herein is stable for at least about 16 months. In some embodiments, the composition disclosed herein is stable for at least about 17 months. In some embodiments, the composition is stable for at least about 18 months. In some embodiments, the composition disclosed herein is stable for at least about 19 months. In some embodiments, the composition disclosed herein is stable for at least about 20 months. In some embodiments, the composition disclosed herein is stable for at least about 21 months. In some embodiments, the composition disclosed herein is stable for at least about 22 months. In some embodiments, the composition disclosed herein is stable for at least about 23 months. In some embodiments, the composition disclosed herein is stable for at least about 24 months (2 years).

In some embodiments, the composition has a pH from about 4.0 to about 8.5. In some embodiments, the composition has a pH from about 4.0 to about 7.5. In some embodiments, the composition has a pH from about 5.0 to about 8.5. In some embodiments, the composition has a pH from about 6.0 to about 7.5. In some embodiments, the composition has a pH from about 7.0 to about 7.5. In some embodiments, the composition has a pH of about 4.0. In some embodiments, the composition has a pH of about 4.5. In some embodiments, the composition has a pH of about 5.0. In some embodiments, the composition has a pH of about 5.5. In some embodiments, the composition has a pH of about 6.0. In some embodiments, the composition has a pH of about 6.5. In some embodiments, the composition has a pH of about 7.0. In some embodiments, the composition has a pH of about 7.5. In some embodiments, the composition has a pH of about 8.0. In some embodiments, the composition has a pH of about 8.5.

Other embodiments and uses will be apparent to one skilled in the art in light of the present disclosures. The following examples are provided merely as illustrative of various embodiments and shall not be construed to limit the present disclosure in any way.

EXAMPLES

Example 1

Pharmacokinetic Studies with Caspofungin Formulations

Experimental Design: Caspofungin was administered to rats at a target dose of 2 mg/kg by nose only inhalation (by deposition) or intravenously (IV) to determine the plasma and tissue concentrations and pharmacokinetics.

Whole blood samples were collected from three animals per time-point at approximately 0.5, 1, 2, 4, 8, 12, 24 and 48 hours and 7 days after dose administration for plasma drug level determination. Rats were anesthetized with 70% $CO_2$/30% air and blood was collected from the retro-orbital plexus and placed into tubes containing anticoagulant (EDTA). Blood samples were placed on ice immediately following collection and processed (i.e., centrifuged) to plasma. The samples were then stored frozen (at approximately $-70°$ C.) until analyzed.

Tissue specimens (lung, liver and kidney) were collected from three animals per time point at 0.5, 2, 24 and 48 hours and 7 days after dose administration. All tissue specimens were stored frozen at approximately $-70°$ C. until analyzed.

Plasma and tissue samples were analyzed for levels of caspofungin using high performance liquid chromatography-mass spectrometry-mass spectrometry (LC-MS-MS) according to methods established for the study.

Exposure of male rats to caspofungin via nose-only inhalation or via intravenous injection resulted in no test-article related mortality; no clinical signs of toxicity; no effects on body weight; and no gross necropsy findings attributable to exposure to the test article.

In Vivo Details: Thirty Sprague-Dawley derived rats [Crl:CD®(CD)Br] were obtained from Charles River Laboratories, Inc., Wilmington, Mass., for use in this study. The rats were 52 days of age (approximately 7.5 weeks) upon arrival. One day following receipt, body weights of the rats ranged from 171 g to 213 g. The animals were held in quarantine for 7 days prior to administration of the test article. Throughout the quarantine period, animals were observed at least once daily for mortality or evidence of a moribund state. Before being released from quarantine, the animals were given a detailed, hand-held physical examination to ensure their health and suitability as test subjects. The test animals were approximately 8.5 weeks old at the start of the first exposure to the test article.

During non-exposure periods of the study all animals were housed in Lab Products Inc., polycarbonate "shoe-box" cages (10.5"×19"×8"), with absorbent hardwood chip bedding. The animals were double housed for the quarantine period), in cages equipped with automatic water and food containers. Animals were double housed for the treatment period in cages equipped with automatic water and food containers. Following group assignment, racks and cages were cleaned and sanitized.

Animal room environmental conditions were recorded at least once daily throughout the quarantine and exposure periods. Temperatures ranged from 20° C. to 21° C. throughout the study, and relative humidity (% RH) values ranged from 46 to 56%. Fluorescent lighting in the animal room was provided on a cycle of 12 hours of light followed by 12 hours of darkness (light from approximately 6:00 a.m. to 6:00 p.m.).

To condition the animals to placement and restraint in the nose-only exposure system and reduce stress during the exposure phase, the animals were acclimated to the holding tubes by placing each rat in a nose-only holding tube for approximately 45 minutes one working day prior to exposure.

The study complied with all applicable sections of the Animal Welfare Act (AWA; Title 9, Code of Federal Regulations), the Public Health Service Policy on Humane Care and Use of Laboratory Animals (National Institutes of Health's Office of Laboratory Animal Welfare, 2002), and the Guide for the Care and Use of Laboratory Animals (National Research Council, 2011). To the extent possible, procedures used in this study were designed to avoid or minimize discomfort, stress, and pain to animals.

The animals were fed Harlan's Certified Global 18% Protein Rodent (2018C). Each certified lot of diet was analyzed for contaminants to ensure that none are present at concentrations that would be expected to interfere with the conduct or purpose of this study. Analytical data from the lots of diet to be used in the study are retained on file. Coarse-filtered City of Chicago water was provided ad libitum to all rats via automatic watering system. Supply water is analyzed periodically for bacterial contamination and chemical composition (e.g., electrolytes, metals, etc.).

Test Article Preparation:

Solution for inhalation: A 10 mg/mL dosing solution was prepared by dissolving 800 mg of caspofungin diacetate powder in 80 mL of 0.9% saline solution. The resulting solution was aseptically filtered and kept refrigerated between 2-8° C. until used.

Solution for IV administration: A 2 mg/mL dosing solution from commercially obtained Cancidas (containing 54.6 mg of caspofungin diacetate) was prepared by a) adding into 10.8 mL of 0.9% saline into the Cancidas vial and swirling gently until the powder dissolved. 10.0 mL of this solution was extracted and added a 25 mL volumetric flask which was diluted to the mark with 0.9% saline and mixed well. The resulting solution was aseptically filtered and kept refrigerated between 2-8° C. until used.

Test Article Dosing: The animals were randomized into two groups of 15 animals based on body weight. Each group was dosed as shown in Table 1 below.

TABLE 1

| Exposure Group | Target Dose | Route | Duration (minutes) | Number of Animals |
|---|---|---|---|---|
| I | 2 mg/kg | Inhalation | 123 | 15 |
| II | 2 mg/kg | IV | N/A | 15 |

The dose targeted for deposition via inhalation was 2 mg/kg and was calculated based on this equation:

$$\text{Deposited dose} = (C \times RMV \times T \times DF)/BW$$

where C is the average caspofungin concentration in the exposure atmosphere during the exposure period, RMV is the respiratory minute volume, T is the exposure time, DF is the deposition fraction (assumed to be 10% per FDA guidelines) and BW is the average animal body weight on exposure day.

The dose for IV administration was calculated based on the body weight of each animal $$\text{Delivered dose} = W \times 2 \text{ mg/kg}$$

where W is animal weight (kg).

Inhalation Exposure Methods:

Inhalation Exposure Laboratory: The inhalation exposure part of the study was conducted in an inhalation facility. The supply air to the laboratories was preconditioned and automatically controlled with a thermostat and humidistat. Each flow-past nose-only inhalation exposure chamber (Lab Products Inc., Seaford, Del.) is comprised of 52 ports. The chambers were encased in an acrylic enclosure to isolate the exposure chamber and protect laboratory personnel. The test atmosphere inlet and exhaust configurations provided a uniform and continuous stream of fresh test atmosphere to the animals undergoing exposure. After flowing out of the supply port, any excess test atmosphere, along with exhaled air, is drawn into the chamber exhaust manifold without entering other ports.

During the inhalation exposure, the animals were restrained in nose-only holding tubes (CH Technologies, USA, Westwood, N.J.). Following confirmation of the correct animal number, each tube was placed in a pre-designated port of the inhalation exposure chamber. Chamber ports were rotated for each exposure; placement for each exposure is documented in the study records. Animal tube loading and unloading and tube insertion and removal from the chamber manifold processes were performed according to laboratory standard operating procedures that are designed to minimize stress to the rats. The rats were observed frequently while restrained to ensure that they remained in the tubes and were not in danger of injury. At the end of each exposure, when the chamber was purged of the test substance (less than one minute), the tubes with the animals were removed. The rats were removed from the tubes and returned to their home cages. The holding tubes were sanitized after each use.

Test Atmosphere Generation: Test atmosphere at the desired concentrations was generated by aerosolizing the test substance and mixing it with compressed filtered air to produce a continuous supply of test atmosphere. Test atmospheres were generated by aerosolizing the test formulation with a commercially available nebulizer using compressed air of breathable quality and which is filtered with a compressed air filter and a carbon adsorber.

Exhaust from the exposure chambers was moved through a high efficiency particulate air (HEPA) filter by a ring compressor and exhausted outside the building. Inlet and exhaust flows to and from the chamber were controlled and continuously monitored by rotometers.

Test Atmosphere Monitoring:

Gravimetric Analysis:

The test atmosphere concentration in the exposure chamber was determined gravimetrically each exposure by collecting test atmosphere samples on filters placed in closed-face filter holders in the breathing zone of the animals. The gravimetric sampling train consisted of a pre-weighed filter in series with a dry-gas meter connected to a constant flow vacuum pump. Samples were collected at a constant flow rate equal to the port flow of the delivery tube. The filter samples were weighed to determine the aerosol mass collected. The dry-gas meter measured the corresponding volume of chamber air sampled and the weight-to-volume ratio was determined to obtain the aerosol mass concentration.

Aerosol Particle Size Distribution:

Aerosol particle size distribution was determined once with a quartz crystal microbalance (QCM) cascade impactor (California Measurements Inc., Sierra Madre, Calif.) equipped with 10 stages to collect size-segregated samples. The mass median aerodynamic diameter (MMAD) and geometric standard deviation (GSD) were calculated from the mass accumulated on each collection stage of the QCM.

Temperature, Relative Humidity and Airflow Rate:

Inhalation Exposure Chamber temperature, relative humidity and airflow rate (liters per minute; LPM) were measured and recorded once during the exposure. The chamber temperature and relative humidity were monitored with a hand-held thermohygrometer (35612 series, Oakton Instruments, Vernon Hills, Ill.).

Intravenous Administration:

Animals in the IV dosing group received a single injection via the tail vein at a dosing volume of 1 mL/kg.

Toxicology Methods:

Moribundity/Mortality Observations and Physical Examinations/Clinical Observations: Prior to initiation of dosing (exposure), animals were observed at least once daily for mortality or evidence of moribundity. A detailed, hand-held physical examination was conducted on all animals once during the quarantine period (prior to randomization). During the treatment period, the animals were observed daily for mortality or evidence of moribundity; these checks were separated by a minimum of four hours. Daily cage-side clinical observations were conducted during exposure, and daily hand-held clinical observations were conducted before and after exposure. Observations included, but were not limited to the following: changes in the skin and fur, eyes, and mucous membranes; effects on the respiratory, circulatory, autonomic and central nervous systems; and effects on somatomotor activity and behavior pattern.

Body Weights and Body Weight Changes: Body weights were determined one day after animal receipt; at randomization; and prior to exposure on Study Day 1, 2, 3 and 7 (as applicable based on scheduled euthanization).

Plasma and Tissue Samples/Necropsy: Whole blood samples were collected from three animals per time-point at approximately 0.5, 1, 2, 4, 8, 12, 24 and 48 hours and 7 days after dose administration for plasma drug level determination. Rats were anesthetized with 70% CO2/30% air and blood was collected from the retro-orbital plexus and placed into tubes containing anticoagulant (EDTA). Blood samples were placed on ice immediately following collection and processed (i.e., centrifuged) to plasma. The samples were then stored frozen (at approximately −70° C.) until analyzed. All study animals surviving to scheduled necropsy were euthanized by an overdose of an intraperitoneal injection of sodium pentobarbital at 35-45 mg/kg. Tissue specimens (lung, liver and kidney) were collected from three animals per time point at 0.5, 2, 24 and 48 hours and 7 days after dose administration. All tissue specimens were stored frozen at approximately −70° C. until analyzed.

Bioanalytical Method and Analysis:

Calibration and Internal Standards: The reference standard, caspofungin acetate (lot number 02220902; Chunghwa Chemical Synthesis & Biotech, Taiwan), was stored at approximately −70° C.; and used without further purification for the preparation of calibration standards and quality control (QC) samples for the determination of caspofungin in plasma and tissue samples collected from this study. The internal standard (caspofungin acetate-d4; lot number 10-GJF-162-1) was stored at −20° C.

Sample Preparation: For the determination of caspofungin in plasma, a 100 µL aliquot from each sample (in a 2 mL centrifuge tube) was mixed with 0.3 mL of acetonitrile (ACN; Spectrum, New Brunswick, N.J.) containing 150 ng of internal standard. After shaking for five minutes, the sample was centrifuged at 4° C. for 10 minutes to remove precipitated proteins and supernatant was transferred to an autosampler tube, diluted with 0.5 mL of water, and vortex-mixed for instrumental analysis.

For the determination of caspofungin in tissue, samples (lung—entire organ; liver—1 gram; kidneys—one organ) were finely cut and extracted for analysis by adding 2.5 mL of ASTM Type I water and shaking for approximately 0.5 hour, after which 2.5 mL of acetonitrile (ACN; Spectrum, New Brunswick, N.J.) were added following by shaking for another 0.5 hour. Subsequently, 100 µL of the supernatant was transferred to a 2 mL centrifuge tube and processed for analysis using the same procedure as for plasma.

Freshly prepared caspofungin standard curves and quality control (QC) samples were analyzed along with the study samples. Instrument calibrators and QC samples were prepared by adding 10 µL of a stock caspofungin solution in ACN/water (v/v 50/50) to 100 µL of blank rat plasma (for both plasma and tissue samples). Calibrator concentrations for plasma specimen analysis were approximately 0.050, 0.10, 0.20, 0.50, 1.0, 2.5, 5.0 and 10 µg/mL; QC samples were prepared at approximately 0.12, 4.0 and 8.0 µg/mL. Calibrator concentrations for tissue specimen analysis were approximately 1, 2, 5, 10, 20, 50 and 100 ng/sample; QC samples were prepared at approximately 2.4, 40 and 80 ng/sample. Calibrators and QC samples were processed for analysis following the procedure described above.

Analytical Equipment and Conditions: Calibrator, QC and study samples were analyzed under LC-MS-MS instrument conditions as detailed in Table 2.

The retention time of caspofungin was approximately 2.3 minutes. Calibration curves were calculated from the linear regression (weighting factor of $1/x^2$) of the caspofungin peak area to internal standard peak area ratios versus caspofungin concentration. Concentration of caspofungin in the samples was determined using the peak area ratio and the regression parameters of the calibration curve. Tissue results in ng were converted to g/g using the amount of tissue extracted and the final extract volume.

TABLE 2

| Instrument Operating Conditions SYSTEM: | 4000 QTrap LC-MS-MS (AB SCIEX, Foster City, CA) equipped with a 1200 HPLC (Agilent Technologies, Wilmington, DE) |
|---|---|
| HPLC CONDITIONS | |
| HPLC Column: | Kinetex Biphenyl 50 mm × 2.1 mm, 5 µm, 100 Å (Phenomenex, Torrance, CA) |
| Column Temperature | 25° C. |
| Injection Volume: | 5 µl |
| Flow Rate: | 300 µL/min |
| Mobile Phase A: | 0.1% formic acid in water |
| Mobile Phase B: | 0.1% formic acid in acetonitrile |

| | Time (minutes) | Mobile Phase A (%) | Mobile Phase B (%) |
|---|---|---|---|
| Program: | 0.00 | 70 | 30 |
| | 0.5 | 70 | 30 |
| | 1.0 | 5 | 95 |
| | 4.0 | 5 | 95 |
| | 4.1 | 70 | 30 |
| | 8.0 | 70 | 30 |

| Run Time: | 8 minutes |
|---|---|
| Retention Time: | Caspofungin and Internal Standard - approximately 2.3 minutes |
| MS-MS CONDITIONS | |
| Scan Type: | MRM |
| Ion Source: | Turbo Spray ESI |
| Ion Spray Voltage: | 5500 Volts |
| Polarity: | Positive |
| Ion Source Temperature: | 550° C. |
| Collision Energy: | Caspofungin and Internal Standard: 20 Volts |
| Ions monitored (Q1→Q3): | Caspofungin: 547.4 → 538.5; Internal Standard: 550.3→ 540.8 |
| Resolution: | Unit |
| Data System: | Analyst ® 1.6.3 (Applied Biosystems/MDS Sciex, Foster City, CA) |

Study Results: The pharmacokinetic experiment was performed as described. The concentrations of caspofungin in plasma, lung, kidney and liver tissues were determined and the results are depicted in the following figures and tables described below.

Figure 2:
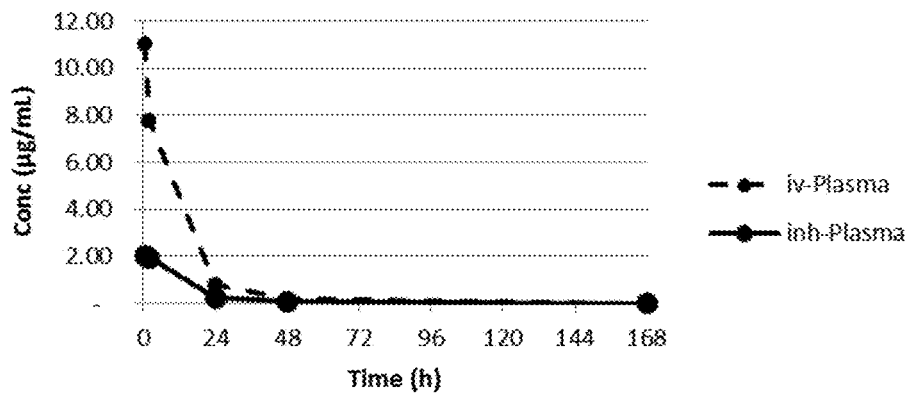
Figure 3:
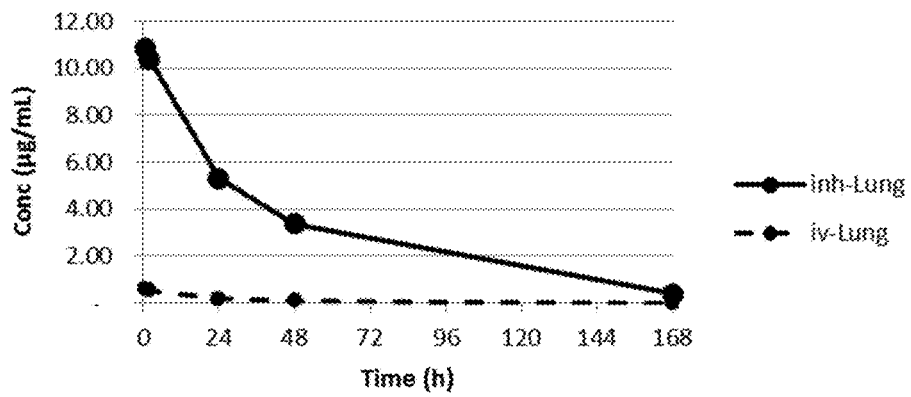
Figure 4:
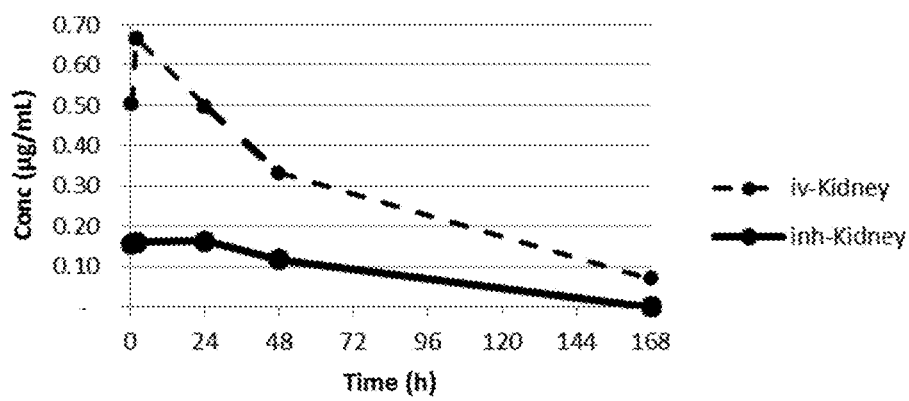
Figure 5:
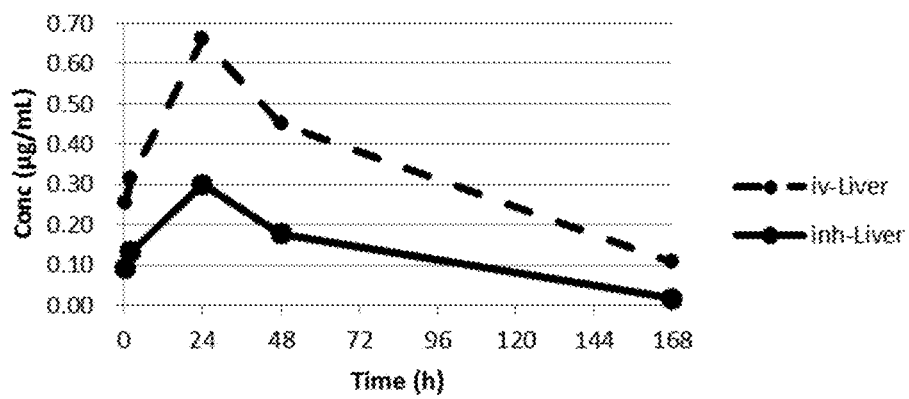
Figure 6:
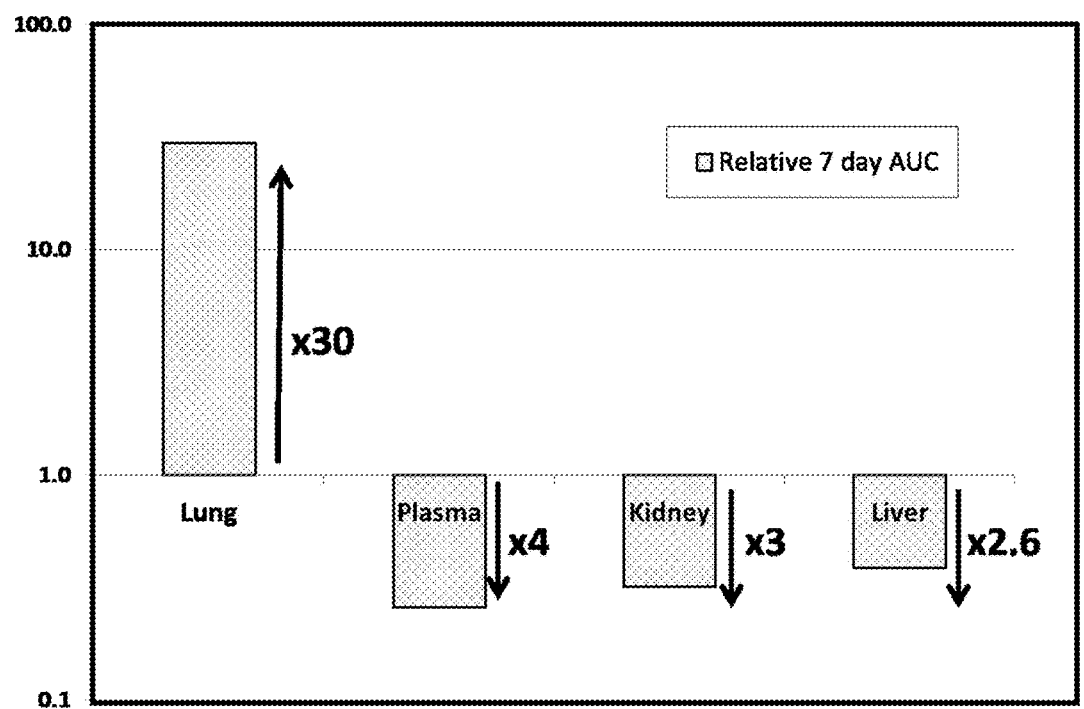

FIG. 1 shows the pharmacokinetics of caspofungin in rat plasma when delivered intravenously (dashed line) or via inhalation (solid line) at 2 mg/kg. FIG. 2 shows the pharmacokinetics of caspofungin in rat plasma when delivered intravenously (dashed line) or via inhalation (solid line) at 2 mg/kg. FIG. 3 shows the pharmacokinetics of caspofungin in rat lung tissue when delivered intravenously (dashed line) or via inhalation (solid line) at 2 mg/kg. FIG. 4 shows the pharmacokinetics of caspofungin in rat kidney tissue when delivered intravenously (dashed line) or via inhalation (solid line) at 2 mg/kg. FIG. 5 shows the pharmacokinetics of caspofungin in rat liver tissue when delivered intravenously (dashed line) or via inhalation (solid line) at 2 mg/kg. FIG. 6 shows the relative weekly exposure per tissue, Inhaled vs IV, from a single 2 mg/kg dose—a ratio of the 7 day AUC for the inhaled route of delivery compared to the 7 day AUC for intravenous administration. Tables 3-5 show the caspofungin concentration as indicated below.

TABLE 3

Caspofungin Concentrations in Rat Lungs

| Time (h) | IV (µg/g) | Inhaled (µg/g) | Inhaled/IV |
|---|---|---|---|
| 0.5 | 0.59 | 10.83 | 18.5 |
| 2 | 0.54 | 10.37 | 19.3 |
| 24 | 0.18 | 5.31 | 29.5 |
| 48 | 0.09 | 3.37 | 37.3 |
| 168 | 0.00 | 0.39 | — |

TABLE 4

Caspofungin Concentration in Rat Tissues Following Inhaled Delivery at a dose of 2 mg/kg

| Time (h) | Lung (µg/g) | Plasma (µg/mL) | Kidney (µg/g) | Liver (µg/g) |
|---|---|---|---|---|
| 0.5 | 10.83 | 2.03 | 0.16 | 0.09 |
| 2 | 10.37 | 1.93 | 0.16 | 0.13 |
| 24 | 5.31 | 0.23 | 0.16 | 0.30 |
| 48 | 3.37 | 0.08 | 0.12 | 0.18 |
| 168 | 0.39 | 0.00 | 0.02 | 0.02 |

TABLE 5

Lung/Tissue Concentrations Ratios Following Inhaled Delivery

| Time (h) | Lung/Plasma | Lung/Kidney | Lung/Liver |
|---|---|---|---|
| 0.5 | 5.3 | 69.1 | 115.0 |
| 2 | 5.4 | 64.7 | 77.8 |
| 24 | 22.9 | 32.4 | 17.6 |
| 48 | 43.8 | 28.8 | 18.9 |
| 168 | — | 26.3 | 23.9 |

Table 6 shows the MIC and MEC for *Aspergillus* spp. isolate susceptibility to caspofungin based from MIC data from Table 4, Caspofungin Acetate FDA Advisory Committee Meeting Background, Merck 2000 and MEC data from Espinel-Ingrof et al. Wild-Type MIC Distributions and Epidemiological Cutoff Values for Caspofungin and *Aspergillus* spp. for the CLSI Broth Microdilution Method, *Antimicrob. Agents Chemo.*, 2011, 55, 6, p 2855-2858.

TABLE 6

| Species | MIC$_{90}$(µg/mL) | | | MEC (µg/mL) | | |
|---|---|---|---|---|---|---|
| | No. isolates | Range | Average[a] | No. isolates | Range | Average[b] |
| Aspergillus fumigatus | 56 | 0.12-4 | 0.25 | 1691 | 0.016-32 | 0.25 |
| Aspergillus flavus | 13 | 0.06-2 | 0.2 | 432 | 0.016-32 | 0.06 |
| Aspergillus nidulans | 13 | 0.2-4 | 0.44 | 192 | 0.032-16 | 0.12 |
| Aspergillus niger | 10 | 0.06-0.5 | 0.14 | 440 | 0.016-2 | 0.06 |
| Aspergillus terrus | 11 | 0.06-.2 | 0.12 | 385 | 0.016-2 | 0.06 |
| Aspergillus versicolor | | | | 75 | 0.032-2 | 0.12 |

[a] Geometric Mean MIC

[b] b. Mode - most frequent minimum effective concentration (MEC)

Table 7 shows the MIC *Candida* spp. isolate susceptibility to caspofungin based from Pfaller et al. Correlation of MIC with Outcome for *Candida* Species Tested against Caspofungin, Anidulafungin, and Micafungin: Analysis and Proposal for Interpretive MIC Breakpoints, *J. Clin Microbiol*, 2008, 46, 8, p 2620-2629.

TABLE 7

| Species | No. isolates | MIC$_{90}$ (µg/mL) |
|---|---|---|
| Candida albicans | 2869 | 0.06 |
| Candida galbrata | 747 | 0.12 |
| Candida tropicalis | 625 | 0.06 |
| Candida krusei | 136 | 0.06 |
| Candida parapsilosis | 759 | 2 |
| Candida guilliermondii | 61 | 2 |

The half-life of caspofungin in the lung, as determined from the studies described herein, is 39 hours i.e. every 39 hours 50% of the remaining drug is eliminated from the lung. A projection of the amount of caspofungin remaining in the lung following a time period equivalent to one half-life is shown below in Table 8. The lung concentration columns show two starting concentrations; one is the concentration measured in the rat lung from the 2 mg/kg dose, the second is the projected concentration that would result from an inhaled dose of 7.2 mg/kg. To be effective the drug concentration should remain above the MIC and MEC. The average MIC and MEC for caspofungin versus *Aspergillus fumigatus*, the species most commonly associated with Aspergillosis is 0.25 µg/L.

TABLE 8

| Hours | Days | Drug Remaining | Lung Concentration (µg/g) | |
|---|---|---|---|---|
| | | | 2 mg/kg | 7.2 mg/kg |
| 0 | 0 | 100% | 10.8 | 39.0 |
| 39 | 1.6 | 50% | 5.42 | 19.5 |
| 78 | 3.3 | 25% | 2.71 | 9.75 |
| 117 | 4.9 | 13% | 1.35 | 4.88 |
| 156 | 6.5 | 6% | 0.68 | 2.44 |
| 195 | 8.1 | 3% | 0.34 | 1.22 |

TABLE 8-continued

| | | | Lung Concentration (µg/g) | |
|---|---|---|---|---|
| Hours | Days | Drug Remaining | 2 mg/kg | 7.2 mg/kg |
| 234 | 9.8 | 2% | 0.17 | 0.61 |
| 273 | 11.4 | 1% | 0.08 | 0.30 |
| 312 | 13.0 | 0.4% | 0.04 | 0.15 |
| 351 | 14.6 | 0.2% | 0.02 | 0.08 |

The measurement of the particles produced during the inhalation experiment showed that they had a MMAD=1.15 µm with a GSD (geometric standard deviation) of 2.67.

Example 2

Comparative Tissue Distribution Studies of Caspofungin

A pharmacokinetic study was performed in rats to investigate the distribution of caspofungin parent compound to the organs most associated with Aspergillosis and compound safety (i.e. lungs, liver and kidney) when delivered either through an intravenous or inhaled route. A comparison with the radiolabeled data from Stone 2004 (Stone, et. al. Disposition of Caspofungin: Role of Distribution in Determining Pharmacokinetics in Plasma, *Antimicrob. Agents Chemo.*, 2004, 48, 3, p 815-823) is shown in Table 9. It is clear that the amounts of caspofungin recovered from the IV dosed study are substantially different from the previously reported caspofungin concentrations. Not only are the distributions significantly different, but they are in no way predictable.

TABLE 9

| | Plasma(µg/mL) | | Lung(µg/g) | | Kidney (µg/g) | | Liver (µg/g) | |
|---|---|---|---|---|---|---|---|---|
| Time(h) | Stone 2004[a] | IV study[b] | Stone 2004[a] | IV study[b] | Stone 2004[a] | IV study[b] | Stone 2004[a] | IV study[b] |
| 0.5 | 11 | 11.03 | 5.12 | 0.59 | 9.15 | 0.50 | 5.03 | 0.25 |
| 2 | 6.1 | 7.72 | 4.50 | 0.54 | 10.60 | 0.67 | 7.04 | 0.31 |
| 24 | 1.74 | 0.80 | 2.44 | 0.18 | 11.40 | 0.50 | 22.20 | 0.66 |

*Both studies dosed at 2 mg/kg
[a]quantities are of radiolabeled compound
[b]quantities are parent caspofungin acetate Example 3

Prophylactic Efficacy of Aerosol Caspofungin in Experimental Pulmonary Aspergillosis The objective of the study is to determine the antifungal efficacy of the caspofungin formulations administered via inhalation therapy in the prophylaxis of invasive pulmonary aspergillosis in rats.

The experimental procedures are performed according to the procedures described in van de Cicogna et. al., *Antimicrob. Agents Chemother.* 1997, 41, 259-261 with further modifications. Caspofungin is used instead of amphotericin B.

The caspofungin formulation used herein include any one of the formulations as described herein, such as those from Example 1, or any one of the following formulations: Formulation 1: caspofungin acetate (4R,5S)-5-[(2-aminoethyl)amino]-$N^2$-(10,12-dimethyl-1 oxotetradecyl)-4-hydroxy-L-ornithine]-5-[(3R)-3-hydroxy-L-ornithine] pneumocandin $B_0$ diacetate) (i.e. 50 mg or 70 mg), sucrose (i.e 34 mg or 54 mg), glacial acetic acid, sodium hydroxide; and Formulation 2: caspofungin acetate (4R,5S)-5-[(2-aminoethyl)amino]-N2-(10,12-dimethyl-loxotetradecyl)-4-hydroxy-L-ornithine]-5-[(3R)-3-hydroxy-L-ornithine] pneumocandin B0 diacetate), glacial acetic acid, sodium hydroxide.

Male Sprague-Dawley rats (Charles River Breeding Laboratories, Wilmington, Mass.) are fed a low-protein diet (8% protein, Dyet, Bethelhem, Pa.) and are given a suitable amount of tetracycline (i.e. 250 mg dissolved in 750 mL of drinking water) to prevent bacterial infection. Furthermore, rats are treated with subcutaneous injections of cortisone acetate (150 mg/kg of body weight) three times a week under anesthesia with enflurane. These injections are either given for two weeks until the day of injection (trial 1) or throughout the duration of the experiment (trial arm 2).

*Aspergillus fumigatus* H11-20 is obtained from a steroid-treated rat dying from spontaneously acquired pulmonary aspergillosis. Other clinical strains of *Aspergillus fumigatus* are also suitable for these experiments. Suitable pores are obtained from subculturing the organism on Sabouraud dextrose for an appropriate time (i.e. 4 to 5 days) and are harvested with 0.02% Tween 80 and washed with sterile saline. The final suspension containing the desired amount of spores/mL, such as $10^7$ spores/mL, is prepared and confirmed by counting with a hemacytometer.

General anesthesia in rats is induced with inhaled enflurane, wherein a suitable amount of the *Aspergillus* spore suspension (i.e., 0.1 mL to deliver $10^6$ spores) is injected with a syringe to the exposed trachea. Wounds are closed surgical staples.

The rats are administered the formulations of caspofungin as described above with an inhalation device, such as a jet nebulizer or an ultrasonic nebulizer, in a glass chamber. Rats are treated at an appropriate time point before infection, such as 48 hours. The estimated amount of drug inhaled by the rats is calculated from the concentration of the product in the chamber, the minute volume of the rats (lung volume times respiratory rate), and exposure time.

For trial 1, rats (8-10 rats in each group) are either treated with a placebo, such as sterile water, or with a suitable dose of caspofungin at a suitable time period before infection (i.e., 48 hours). Immunosuppressive treatments with cortisone acetate are discontinued after time of infection. Rats in this group are monitored for survival on daily basis for an appropriate amount of time (i.e., 7 days).

For trial 2, rats (8-10 rats in each group) are either treated with a placebo, such as sterile water or with an appropriate dose of caspofungin at a suitable time period before infection (i.e., 48 hours). Immunosuppressive treatments with cortisone acetate are continued for the duration of the experiment after infection (i.e., 14 days).

The outcome variables used to assess efficacy of this study include but are not limited: survival of the infected rats during therapy and after termination of therapy and caspofungin concentration in the lung tissue and other organs (liver, kidney, spleen, and pancreas) and plasma.

Example 4

Antifungal Efficacy of Caspofungin in Treatment of Experimental Pulmonary Aspergillosis in Transiently Neutropenic Rats The objective of the study is to determine the antifungal efficacy of the caspofungin formulations administered via inhalation therapy in the treatment of invasive pulmonary aspergillosis in transiently neutropenic rats.

The experimental procedures are performed according to the procedures described in van de Sande et. al., *Antimicrob. Agents Chemother.* 2008, 52, 1345-1350 with further modifications.

The caspofungin formulation used herein include any one of the formulations as described herein, such as those from Example 1, or any one of the following formulations: Formulation 1: caspofungin acetate (4R,5S)-5-[(2-aminoethyl)amino]-$N^2$-(10,12-dimethyl-1 oxotetradecyl)-4-hydroxy-L-ornithine]-5-[(3R)-3-hydroxy-L-ornithine] pneumocandin $B_0$ diacetate) (i.e. 50 mg or 70 mg), sucrose (i.e 34 mg or 54 mg), glacial acetic acid, sodium hydroxide; and Formulation 2: caspofungin acetate (4R,5S)-5-[(2-aminoethyl)amino]-N2-(10,12-dimethyl-loxotetradecyl)-4-hydroxy-L-ornithine]-5-[(3R)-3-hydroxy-L-ornithine] pneumocandin B0 diacetate), glacial acetic acid, sodium hydroxide.

A clinical strain of *Aspergillus fumigatus* is obtained from a hemato-oncological patient with pulmonary aspergillosis. The strain is passed through neutropenic rats and maintained on Sabourand agar slants in order to maintain the strain's virulence. The minimal inhibitory concentration (MIC) and minimal effective concentration (MEC) of the strain used for this experiment against caspofungin are determined accordingly.

Infection Model and Antifungal Treatment

The rat model of aerogenic left-sided invasive pulmonary aspergillosis as described in van de Sande et. al., *Antimicrob. Agents Chemother.* 2008, 52, 1345-1350 is used. Neutropenia is induced by intraperitoneal administration of a suitable dose of cyclophosphamide, such as 75 mg/kg, and is administered before inoculation (i.e., 5 days) followed by administration of a suitable dose prior to inoculation (i.e., 60 mg/kg 1 day before inoculation) and several doses following inoculation (i.e., 50, 40, and 30 mg/kg on days 3, 7, and 11 after fungal inoculation).

Fungal infection is established by intubation of the left main bronchus while the rats are under general anesthesia. A cannula is passed through the tube, and the left lobe is inoculated with the appropriate amount of aspergillosis, such as $6\times10^4$ conidia.

Antifungal therapy is initiated at a suitable time point after inoculation, such as 16 h, 24 h, or 72 h after inoculation. The rats are administered the formulations of caspofungin as described above with an inhalation device, such as a jet nebulizer or an ultrasonic nebulizer, in an appropriate dose (i.e., 4 mg/kg or 10 mg/kg) and suitable dosing schedule, such as once a day, once every two days, or once every three days. The antifungal therapy is continued for a suitable amount of time, such as 7 days, 14 days, or 21 days.

Outcome Variables

The outcome variables used to assess efficacy include but not limited to following: survival of the infected rats during therapy and after termination of therapy, pulmonary infarct score, lung weight, residual, fungal burden (log CFU/gram), fungal growth (log CFU/gram) in bronchoalveolar lavage fluid, computerized tomograph (CT) scores, galactamannan index (GMI), and histopathology.

Example 5

Antifungal Efficacy of Caspofungin for Prophylaxis of Experimental Pulmonary Aspergillosis in Transiently Neutropenic Rats The objective of the study is to determine the antifungal efficacy of the caspofungin formulations administered via inhalation therapy in the prophylaxis of invasive pulmonary aspergillosis in transiently neutropenic rats.

The experimental procedures are performed according to the procedures described in van de Sande et. al., *Antimicrob. Agents Chemother.* 2008, 52, 1345-1350 with further modifications.

The caspofungin formulation used herein include any one of the formulations as described herein, such as those from Example 1, or any one of the following formulations: Formulation 1: caspofungin acetate (4R,5S)-5-[(2-aminoethyl)amino]-$N^2$-(10,12-dimethyl-1 oxotetradecyl)-4-hydroxy-L-ornithine]-5-[(3R)-3-hydroxy-L-ornithine] pneumocandin $B_0$ diacetate) (i.e. 50 mg or 70 mg), sucrose (i.e 34 mg or 54 mg), glacial acetic acid, sodium hydroxide; and Formulation 2: caspofungin acetate (4R,5S)-5-[(2-aminoethyl)amino]-N2-(10,12-dimethyl-loxotetradecyl)-4-hydroxy-L-ornithine]-5-[(3R)-3-hydroxy-L-ornithine] pneumocandin B0 diacetate), glacial acetic acid, sodium hydroxide.

To assess the efficacy of caspofungin inhalation therapy for the prophylaxis of pulmonary aspergillosis in a transiently neutropenic rat model, the same methods used for the assessing the therapeutic efficacy as described in Example 4 are utilized with the following exceptions: caspofungin administration via inhalation is started at a suitable time period before inoculation (i.e., 24 to 48 hours before infection); and a lower load of administered inoculum is administered in order to simulate the low initial tissue burden of *A. fumigatus*. Similar outcome variables as described in Example 4 are used to assess efficacy.

What is claimed is:

1. A method of treating a fungal infection in the pulmonary system of a subject in need thereof comprising administering to the subject an inhalation composition comprising caspofungin, a polymorph, pharmaceutically acceptable salt, hydrate, or solvate thereof, wherein the inhalation composition is an aqueous solution essentially free of mannitol, and wherein the inhalation composition is administered as droplets or particles having a mass median aerodynamic diameter (MMAD) from about 0.5 μm to about 10 μm.

2. The method of claim 1, wherein the inhalation composition is essentially free of sugar alcohol.

3. The method of claim 1, wherein the inhalation composition is essentially free of sugar alcohol or sugar.

4. The method of claim 1, wherein the pharmaceutically acceptable salt of caspofungin is an acetate salt.

5. The method of claim 1, wherein the administration of the inhalation composition provides a lung tissue concentration of caspofungin or the polymorph, pharmaceutically acceptable salt, hydrate, or solvate thereof that is from about 1-fold to about 100-fold greater than intravenous administration at the same delivery dose.

6. The method of claim 5, wherein the lung tissue concentration of caspofungin or the polymorph, pharmaceutically acceptable salt, hydrate, or solvate thereof is greater than intravenous administration at the same delivery dose for about 0.5 hour to about 168 hours.

7. The method of claim 1, wherein the administration of the inhalation composition provides a lung tissue concentration of caspofungin or the polymorph, pharmaceutically acceptable salt, hydrate, or solvate thereof that is from about 1-fold to about 50-fold greater than intravenous administration at the same delivery dose.

8. The method of claim 7, wherein the lung tissue concentration of caspofungin or the polymorph, pharmaceutically acceptable salt, hydrate, or solvate thereof is greater than intravenous administration at the same delivery dose for about 0.5 hour to about 168 hours.

9. The method of claim 1, wherein the administration of the inhalation composition provides a concentration of caspofungin or the polymorph, pharmaceutically acceptable salt, hydrate, or solvate thereof in the lung that is from about 1-fold greater to about 1000-fold greater than a concentration of caspofungin or the polymorph, pharmaceutically acceptable salt, hydrate, or solvate thereof in the liver, kidney, spleen, pancreas or plasma.

10. The method of claim 9, wherein the concentration of caspofungin or the polymorph, pharmaceutically acceptable salt, hydrate, or solvate thereof in the lung is greater than the concentration of caspofungin or the polymorph, pharmaceutically acceptable salt, hydrate, or solvate thereof in the liver, kidney, spleen, pancreas or plasma for about 0.5 hour to about 168 hours.

11. The method of claim 1, wherein the administration of the inhalation composition provides a concentration of caspofungin or the polymorph, pharmaceutically acceptable salt, hydrate, or solvate thereof in the lung that is from about 1-fold greater to about 150-fold greater than a concentration of caspofungin or the polymorph, pharmaceutically acceptable salt, hydrate, or solvate thereof in the liver, kidney, spleen, pancreas or plasma.

12. The method of claim 11, wherein the concentration of caspofungin or the polymorph, pharmaceutically acceptable salt, hydrate, or solvate thereof in the lung is greater than the concentration of caspofungin or the polymorph, pharmaceutically acceptable salt, hydrate, or solvate thereof in the liver, kidney, spleen, pancreas or plasma for about 0.5 hour to about 168 hours.

13. The method of claim 1, wherein the administration of the inhalation composition provides a concentration of caspofungin or the polymorph, pharmaceutically acceptable salt, hydrate, or solvate thereof in the lung that is above the minimum inhibitory concentration (MIC) or the minimum effective concentration (MEC) for about 3 hours after administration.

14. The method of claim 1, wherein the administration of the inhalation composition provides a concentration of caspofungin or the polymorph, pharmaceutically acceptable salt, hydrate, or solvate thereof in the lung that is above the minimum inhibitory concentration (MIC) or the minimum effective concentration (MEC) for about 12 hours after administration.

15. The method of claim 1, wherein the administration of the inhalation composition provides a concentration of caspofungin or the polymorph, pharmaceutically acceptable salt, hydrate, or solvate thereof in the lung that is above the minimum inhibitory concentration (MIC) or the minimum effective concentration (MEC) for about 24 hours after administration.

16. The method of claim 1, wherein the administration of the inhalation composition provides a concentration of caspofungin or the polymorph, pharmaceutically acceptable salt, hydrate, or solvate thereof in the lung that is above the minimum inhibitory concentration (MIC) or the minimum effective concentration (MEC) for about 48 hours after administration.

17. The method of claim 13, wherein the minimum inhibitory concentration (MIC) is from about 0.001 μg/mL to about 128 μg/mL.

18. The method of claim 13, wherein the minimum inhibitory concentration (MIC) is from about 0.001 μg/mL to about 32 μg/mL.

19. The method of claim 13, wherein the minimum effective concentration (MEC) is from about 0.001 μg/mL to about 128 μg/mL.

20. The method of claim 13, wherein the minimum inhibitory concentration (MEC) is from about 0.001 μg/mL to about 32 μg/mL.

21. The method of claim 1, wherein the inhalation composition is administered with an inhalation device selected from a jet nebulizer, ultrasonic wave nebulizer, high efficiency nebulizer, heat vaporizer, soft mist inhaler, thermal aerosol inhaler, or electrohydrodynamic-based solution misting inhaler.

22. The method of claim 1, wherein the inhalation composition is administered by the inhalation device as droplets or particles having a mass median aerodynamic diameter (MMAD) from about 1 μm to about 5 μm.

23. The method of claim 1, wherein the half-life of the caspofungin, or a polymorph, pharmaceutically acceptable salt, hydrate, or solvate thereof in the lung is about 1 hour to about 50 hours.

24. The method of claim 1, wherein the half-life of the caspofungin, or a polymorph, pharmaceutically acceptable salt, hydrate, or solvate thereof in the lung is about 20 hours to about 50 hours.

25. The method of claim 1, wherein the inhalation composition is stable from at about −20° C. to about 25° C.

26. The method of claim 1, wherein the inhalation composition is stable for at least about 6 months.

27. The method of claim 1, wherein the inhalation composition has a pH from about 4.0 to about 7.5.

28. The method of claim 1, wherein the method is for treating a fungal infection caused by *Candida* sp., and/or by *Aspergillus* sp., and/or by *Pnenmocystis jirovecii*.

* * * * *

UNITED STATES PATENT AND TRADEMARK OFFICE
CERTIFICATE OF CORRECTION

| | | |
|---|---|---|
| PATENT NO. | : 9,675,659 B2 | Page 1 of 1 |
| APPLICATION NO. | : 15/241645 | |
| DATED | : June 13, 2017 | |
| INVENTOR(S) | : David M. Ryckman and Iching G. Yu | |

It is certified that error appears in the above-identified patent and that said Letters Patent is hereby corrected as shown below:

In the Claims

Column 112, Line 55:
Change "28. The method of claim 1, wherein the method is for treating a fungal infection caused by Candida sp., and/or by Aspergillus sp., and/or by Pnenmocystis jirovecii." to --"28. The method of claim 1, wherein the method is for treating a fungal infection caused by Candida sp., and/or by Aspergillus sp., and/or by Pneumocystis jirovecii."--

Signed and Sealed this
First Day of August, 2017

Joseph Matal
*Performing the Functions and Duties of the
Under Secretary of Commerce for Intellectual Property and
Director of the United States Patent and Trademark Office*